United States Patent
Ogawa et al.

(10) Patent No.: US 9,089,633 B2
(45) Date of Patent: Jul. 28, 2015

(54) ARTIFICIAL HEART DEVICE

(75) Inventors: Daisuke Ogawa, Nagano (JP); Hideki Kanebako, Nagano (JP); Akihiro Matsuda, Nagano (JP)

(73) Assignee: SUN MEDICAL TECHNOLOGY RESEARCH CORPORATION, Nagano (JP)

( * ) Notice: Subject to any disclaimer, the term of this patent is extended or adjusted under 35 U.S.C. 154(b) by 663 days.

(21) Appl. No.: 13/306,077

(22) Filed: Nov. 29, 2011

(65) Prior Publication Data

US 2012/0142998 A1 Jun. 7, 2012

(30) Foreign Application Priority Data

Dec. 3, 2010 (JP) ................................. 2010-270912

(51) Int. Cl.
*A61M 1/10* (2006.01)
*A61M 1/12* (2006.01)

(52) U.S. Cl.
CPC ............... *A61M 1/10* (2013.01); *A61M 1/1086* (2013.01); *A61M 1/122* (2013.01); *A61M 1/125* (2013.01); *A61M 2205/50* (2013.01); *A61M 2205/52* (2013.01)

(58) Field of Classification Search
CPC ....... A61M 1/10; A61M 1/101; A61M 1/086; A61M 1/122; A61M 1/86
USPC ............................... 600/16, 17; 623/3.1, 3.28
See application file for complete search history.

(56) References Cited

U.S. PATENT DOCUMENTS

| | | | |
|---|---|---|---|
| 6,132,363 A | 10/2000 | Freed et al. | |
| 6,183,412 B1 | 2/2001 | Benkowski et al. | |
| 6,605,032 B2 * | 8/2003 | Benkowski et al. | 600/16 |
| 6,652,447 B2 | 11/2003 | Benkowski et al. | |
| 6,949,066 B2 | 9/2005 | Bearnson et al. | |
| 2001/0041934 A1* | 11/2001 | Yamazaki et al. | 623/3.13 |
| 2007/0282298 A1 | 12/2007 | Mason | |
| 2008/0114339 A1 | 5/2008 | McBride et al. | |
| 2009/0292222 A1* | 11/2009 | Ferren et al. | 600/549 |
| 2011/0071338 A1 | 3/2011 | McBride et al. | |
| 2011/0112354 A1 | 5/2011 | Nishimura et al. | |

FOREIGN PATENT DOCUMENTS

| | | |
|---|---|---|
| EP | 1847281 A1 | 10/2007 |
| JP | 2009297174 A | 12/2009 |

(Continued)

OTHER PUBLICATIONS

European Search Report corresponding to EP11191525, dated Mar. 7, 2012.

*Primary Examiner* — Brian T Gedeon
*Assistant Examiner* — Ankit Tejani
(74) *Attorney, Agent, or Firm* — Lowe Hauptman & Ham, LLP

(57) ABSTRACT

An artificial heart device includes: a blood pump which assists flow of blood in a heart; a blood pump control part which controls the blood pump; a first data processing part which performs first data processing on at least one data in a first period out of operation data on the blood pump, operation data on a cool sealing unit which circulates lubrication fluid in the blood pump, biological data corresponding to a state of a patient and operation data on a battery; and a TR data storing part which stores data after the first data processing in association with date-and-time data corresponding to date and time at which the data is stored each time the first period elapses, wherein the data stored in the TR data storing part is retrievable.

8 Claims, 17 Drawing Sheets

(56) References Cited

FOREIGN PATENT DOCUMENTS

| WO | 9916481 | A1 | 4/1999 |
| WO | 9917819 | A1 | 4/1999 |
| WO | 2007053881 | A1 | 5/2007 |
| WO | 2007112033 | A2 | 10/2007 |

* cited by examiner

| | date and time data | |
|---|---|---|
| blood pump operation data | rotational speed (instruction value) | |
| | rotational speed (actually measured value) | |
| | rotational speed maximum value | |
| | rotational speed minimum value | |
| | power consumption | |
| | power consumption maximum value | |
| | power consumption minimum value | |
| | ............... | |
| cool sealing unit operation data | flow passage pressure (instruction value) | |
| | rotational speed (actually measured value) | |
| | rotational speed maximum value | |
| | rotational speed minimum value | |
| | power consumption | |
| | power consumption maximum value | |
| | power consumption minimum value | |
| | flow passage pressure (actually measured value) | |
| | flow passage pressure maximum value | |
| | flow passage pressure minimum value | |
| | ............... | |
| battery operation data | voltage | |
| | ............... | |
| ............... | ............... | |

FIG.8

| date and time data ||
|---|---|
| blood pump operation data | rotational speed |
| | power consumption |
| | ............... |
| cool sealing unit operation data | flow passage pressure |
| | rotational speed |
| | power consumption |
| | ............... |
| battery operation data | voltage |
| | ............... |
| event state | detected event |
| ............... | ............... |

FIG.9

| |
|---|
| battery mounting and removal event |
| blood pump rotational speed detection event |
| blood pump power consumption detection event |
| cool-sealing-unit rotational speed detection event |
| cool-sealing-unit power consumption detection event |
| cool-sealing-unit flow passage pressure detection event |
| cool-sealing-unit disconnection detection event |
| blood pump start event |
| blood pump stop event |
| operation event |
| ·········· |

FIG.10

| | |
|---|---|
| blood pump operation data | rotational speed (instruction value) |
| | rotational speed (actually measured value) |
| | power consumption |
| | ............... |
| cool sealing unit operation data | flow passage pressure (instruction value) |
| | rotational speed (actually measured value) |
| | power consumption |
| | flow passage pressure (actually measured value) |
| | ............... |
| battery operation data | voltage |
| | ............... |
| event state | detected event |
| ............... | ............... |

FIG.11

ARTIFICIAL HEART DEVICE

RELATED APPLICATIONS

The present application is based on, and claims priority from, Japanese Application Number 2010-270912, filed Dec. 3, 2010, the disclosure of which is hereby incorporated by reference herein in its entirety.

TECHNICAL FIELD

The present invention relates to an artificial heart device or the like which assists flow of blood in a heart.

BACKGROUND OF THE INVENTION

Along with the progress of medical technology in recent years, the number of cases has increased where cardiopathy can be cured. On the other hand, with respect to serious cardiopathy, there may also be a case where the only way to cure such cardiopathy is with a heart transplant. In a case where a patient waiting for a heart transplant chooses a heart transplant, he has to wait for a donor who is compatible with the patient. Accordingly, when the patient cannot be subjected to the heart transplant as early as possible, this may seriously ill-affect the maintaining of the life of the patient.

Under such circumstances, recently, aiming at BTT (Bridge To Transplant), there has been proposed a method where an artificial heart device is mounted a patient waiting for a heart transplant, and the circulation of blood of the patient is assisted by operating the artificial heart device. With the use of such an artificial heart device, the patient waiting for a heart transplant can wait for a donor who is compatible with the patient for a long period. Further, due to the enhancement of stability, reliability and the like of an artificial heart device, attention has been focused on the use of an artificial heart device which aims at BTR (Bridge To Recovery) which allows a patient to seek for the recovery of functions of his own heart. In fact, there have been many reports on examples in which a patient has recovered functions of his own heart by mounting an artificial heart device on his body.

A technique relating to such an artificial heart device is disclosed in patent document 1, for example. Patent document 1 discloses a technique where physiological parameters corresponding to a state of a patient and operation parameters corresponding to a state of a blood pump which constitutes an artificial heart device are measured and the artificial heart device is controlled based on the interrelation between these parameters.

On the other hand, along with the prolongation of a period during which a patient who mounts an artificial heart device on his body and waits for a heart transplant can enjoy a life substantially equal to a life which a person having no cardiopathy enjoys, it is necessary to periodically confirm an operation state of the artificial heart device or to periodically perform other maintenance operations. A technique relating to such maintenance of an artificial heart device is disclosed in patent document 2 and patent document 3, for example. Patent document 2 and patent document 3 disclose a technique where parameters of a blood pump are continuously accumulated in a memory and the stored parameters can be outputted to the outside.

PRIOR ART DOCUMENT

Patent document

Patent document 1: U.S. Pat. No. 6,949,066
Patent document 2: U.S. Pat. No. 6,183,412
Patent document 3: U.S. Pat. No. 6,652,447

SUMMARY OF THE INVENTION

Problem to be Solved by the Invention

To ensure a patient who mounts the artificial heart device described in patent document 1 on his body to lead an ordinary life over a long period, the maintenance of the artificial heart device described in patent document 2 and patent document 3 becomes necessary. In patent document 2 and patent document 3, however, parameters of the blood pump are accumulated in a memory simply as so-called real time data. Accordingly, the accumulation of real time data over a long period implies that it is necessary to mount a memory having large capacity on the artificial heart device. This mounting of the memory of the large capacity on the artificial heart device gives rise to a drawback that the miniaturization of the artificial heart device is impeded, and QOL (Quality of Life: hereinafter referred to as QOL) of a patient cannot be enhanced. Accordingly, it becomes difficult to provide a portable artificial heart device which can be driven by a battery thus making the enhancement of QOL of a patient difficult.

On the other hand, when real time data is accumulated in the memory after simply thinning real time data, there is a possibility that data analysis cannot be performed sufficiently. Further, when a certain abnormality occurs, there exists a possibility that it is impossible to determine whether a trouble is derived from a patient or from an artificial heart device. Accordingly, there exists a drawback that a lifetime of the artificial heart device cannot be prolonged or probability of the occurrence of detected abnormalities cannot be lowered and hence, reliability of the artificial heart device cannot be enhanced.

The present invention has been made in view of the above-mentioned technical drawbacks. According to some modes of the present invention, it is an object of the present invention to provide an artificial heart device or the like which can contribute to the enhancement of QOL of patients and the reliability of the artificial heart device.

Means for Solving the Task (1) According to a first mode of the present invention, there is provided an artificial heart device which includes: a blood pump which assists flow of blood in a heart; a blood pump control part which controls the blood pump; one or a plurality of sensors which are provided for acquiring operation data on the blood pump, operation data on a cool sealing unit which circulates lubrication fluid in the blood pump, biological data corresponding to a state of a patient who mounts the blood pump on his body or operation data on a power source which supplies electricity to the artificial heart device; a first data processing part which performs first data processing on at least one data in a first period out of the operation data on the blood pump, the operation data on the cool sealing unit, the biological data and operation data on the power source; and a first data storing part which stores data after the first data processing in association with date-and-time data corresponding to date and time at which the data is stored each time the first period elapses, wherein the data stored in the first data storing part is retrievable.

According to this mode, representative data in the first period is stored by processing the operation data on the blood pump or the like and hence, a data size can be reduced whereby an operation state of the artificial heart device can be analyzed later even when the artificial heart device is operated over a long period. Accordingly, it becomes possible to understand an operation state of the artificial heart device without imposing a burden on the patient thus contributing to the enhancement of QOL of a patient and the reliability of the artificial heart device.

(2) According to a second mode of the present invention, in the first mode of the present invention, the first data processing includes at least one of calculation processing for acquiring an average value by calculation in the first period, calculation processing for acquiring a maximum value by calculation in the first period, calculation processing for acquiring a minimum value by calculation in the first period, and predetermined filter processing.

According to this mode, in addition to the above-mentioned advantageous effects, it becomes possible to understand an operation state of the artificial heart device more easily.

(3) According to a third mode of the present invention, in the first mode or the second mode of the present invention, the artificial heart device further includes: a second data processing part which performs second data processing on at least one data out of the operation data on the blood pump, the operation data on the cool sealing unit, the biological data, and the operation data on the power source; and a second data storing part which stores, out of data after the second data processing, data in a second period before and after detection timing of a predetermined event in association with the date-and-time data corresponding to date and time at which the data is stored, and the data stored in the second data storing part is retrievable.

According to this mode, in addition to the above-mentioned advantageous effects, even when a certain phenomenon cannot be analyzed using only data after first data processing, such a phenomenon can be analyzed by merely accumulating the detailed data only on minimum required portions. Accordingly, even when the artificial heart device is operated for a long period, that is, several days to several months, it becomes possible to understand an event occurrence state more precisely by analyzing data after second data processing.

(4) According to a fourth mode of the present invention, there is provided an artificial heart device which includes: a blood pump which assists flow of blood in a heart; a blood pump control part which controls the blood pump; one or a plurality of sensors which are provided for acquiring operation data on the blood pump, operation data on a cool sealing unit which circulates lubrication fluid in the blood pump, biological data corresponding to a state of a patient who mounts the blood pump on his body or operation data on a power source which supplies electricity to the artificial heart device; a second data processing part which performs second data processing on at least one data out of the operation data on the blood pump, the operation data on the cool sealing unit, the biological data and operation data on the power source; and a second data storing part which stores, out of data after the second data processing, data in a second period before and after detection timing of a predetermined event in association with the date-and-time data corresponding to date and time at which the data is stored, and the data stored in the second data storing part is retrievable.

According to this mode, unlike a case where operation data on the blood pump or the like is stored irrespective of detection timing of an event, it is sufficient to merely accumulate detailed data only on minimum required portions. Accordingly, even when the artificial heart device is operated for a long period, that is, several days to several months, it becomes possible to understand an event occurrence state more precisely by analyzing data after second data processing.

(5) According to a fifth mode of the present invention, in the third mode or the fourth mode of the present invention, the second data processing includes at least one of calculation processing for acquiring an average value by calculation, calculation processing for acquiring a maximum value_by calculation, calculation processing for acquiring a minimum value by calculation, and predetermined filter processing.

According to this mode, in addition to the above-mentioned advantageous effects, it becomes possible to understand the event occurrence state still more precisely.

(6) According to a sixth mode of the present invention, in any one of the first mode to the fifth mode of the present invention, the artificial heart device further includes: an event detecting part which detects an event based on at least one of the operation data on the blood pump, the operation data on the cool sealing unit, the biological data, the operation data on the power source, mounting and removal data which is updated at the time of mounting or removing the power source, and manipulation data on a manipulation part for controlling the artificial heart device; and a third data storing part which stores event data corresponding to the event detected by the event detecting part in association with the date and time data, and the data stored in the third data storing part is retrievable.

According to this mode, in addition to the above-mentioned advantageous effects, the record of the occurrence of events can be analyzed later and hence, the present invention can contribute to the further enhancement of the QOL of a patient and the reliability of the artificial heart device by analyzing the event occurrence states.

(7) According to a seventh mode of the present invention, in the fourth mode or the fifth mode of the present invention, the artificial heart device further includes: an event detecting part which detects an event based on at least one of the operation data on the blood pump, the operation data on the cool sealing unit, the biological data, the operation data on the power source, mounting and removal data which is updated at the time of mounting or removing the power source, and manipulation data on a manipulation part for controlling the artificial heart device, and the second data storing part stores, out of the data after the second data processing, the data in a second period before and after detection timing of the event detected by the event detecting part in association with the date and time data corresponding to date and time at which the data is stored.

According to this mode, in addition to the above-mentioned advantageous effects, unlike a case where operation data on the blood pump or the like is stored irrespective of detection timing of an event, it is sufficient to merely accumulate detailed data only on minimum required portions. Accordingly, even when the artificial heart device is operated for a long period, that is, several days to several months, it becomes possible to understand an event occurrence state more precisely by analyzing data after second data processing.

(8) According to an eighth mode of the present invention, there is provided an artificial heart device which includes: a blood pump which assists flow of blood in a heart; a blood pump control part which controls the blood pump; one or a plurality of sensors which are provided for acquiring operation data on the blood pump, operation data on a cool sealing unit which circulates lubrication fluid in the blood pump, biological data corresponding to a state of a patient who mounts the blood pump on his body or operation data on a power source which supplies electricity to the artificial heart device; an event detecting part which detects an event based on at least one data out of the operation data on the blood pump, the operation data on the cool sealing unit, the biological data, operation data on the power source, mounting and removal data which is updated at the time of mounting or removing the power source, and manipulation data on a manipulation part for controlling the artificial heart device; and a third data storing part which stores event data corresponding to the event detected by the event detecting part in association with the date and time data, and the data stored in the third data storing part is retrievable.

According to this mode, the record of the occurrence of events can be analyzed later and hence, the present invention can contribute to the further enhancement of the QOL of a patient and the reliability of the artificial heart device by analyzing the event occurrence states.

(9) According to a ninth mode of the present invention, in any one of the first mode to the eighth mode of the present invention, out of the operation data on the blood pump, the operation data on the cool sealing unit, the biological data and the operation data on the power source, at least one data can be outputted.

According to this mode, in addition to the above-mentioned advantageous effects, a present operation state of the artificial heart device can be monitored and hence, it becomes possible to easily understand a current state of the artificial heart device when the occurrence of an event was detected in the past.

(10) According to a tenth mode of the present invention, in any one of the first mode to the ninth mode of the present invention, the artificial heart device further includes a fourth data storing part which stores at least one of information on a patient who mounts the blood pump on his body, a identification number given to a constitutional element of the artificial heart device, the time the artificial heart device was used, an identification number given to the power source, the time the power source was used, and the number of times of charge to the power source, and data stored in the fourth data storing part is retrievable.

According to this mode, in addition to the above-mentioned advantageous effects, it becomes possible to manage a state where a patient uses the artificial heart device and a use state of respective parts of the artificial heart device including the power source. Accordingly, a burden imposed on the patient can be reduced, and the reliability of the artificial heart device can be further enhanced.

(11) According to an eleventh mode of the present invention, in any one of the first mode to the tenth mode of the present invention, the artificial heart device includes: the cool sealing unit which circulates lubrication fluid in the blood pump; and a circulation path along which the lubrication fluid is circulated.

According to this mode, it is possible to provide the artificial heart device which further includes the cool sealing unit and hence, in addition to the above-mentioned effect, it is possible to enhance the QOL of a patient who mounts the artificial heart device on his body for a long period and the reliability of the device per se while suppressing coagulation of blood or generation of heat in the blood pump.

BRIEF DESCRIPTION OF THE DRAWINGS

FIG. 8 is a view showing one example of TR data according to the embodiment of the present invention.

FIG. 9 is a view showing one example of SS data according to the embodiment of the present invention.

FIG. 10 is a view showing one example of EV data according to the embodiment of the present invention.

FIG. 11 is a view showing one example of RT data according to the embodiment of the present invention.

MODE FOR CARRYING OUT THE INVENTION

Hereinafter, an embodiment of the present invention is explained in detail in conjunction with drawings. The embodiment explained hereinafter does not unduly limit contents of the present invention described in Claims. Further, it is not limited that all constitutions explained hereinafter are indispensable constitutional elements for overcoming drawbacks of the present invention.

[Artificial Heart Device]

Figure 1:
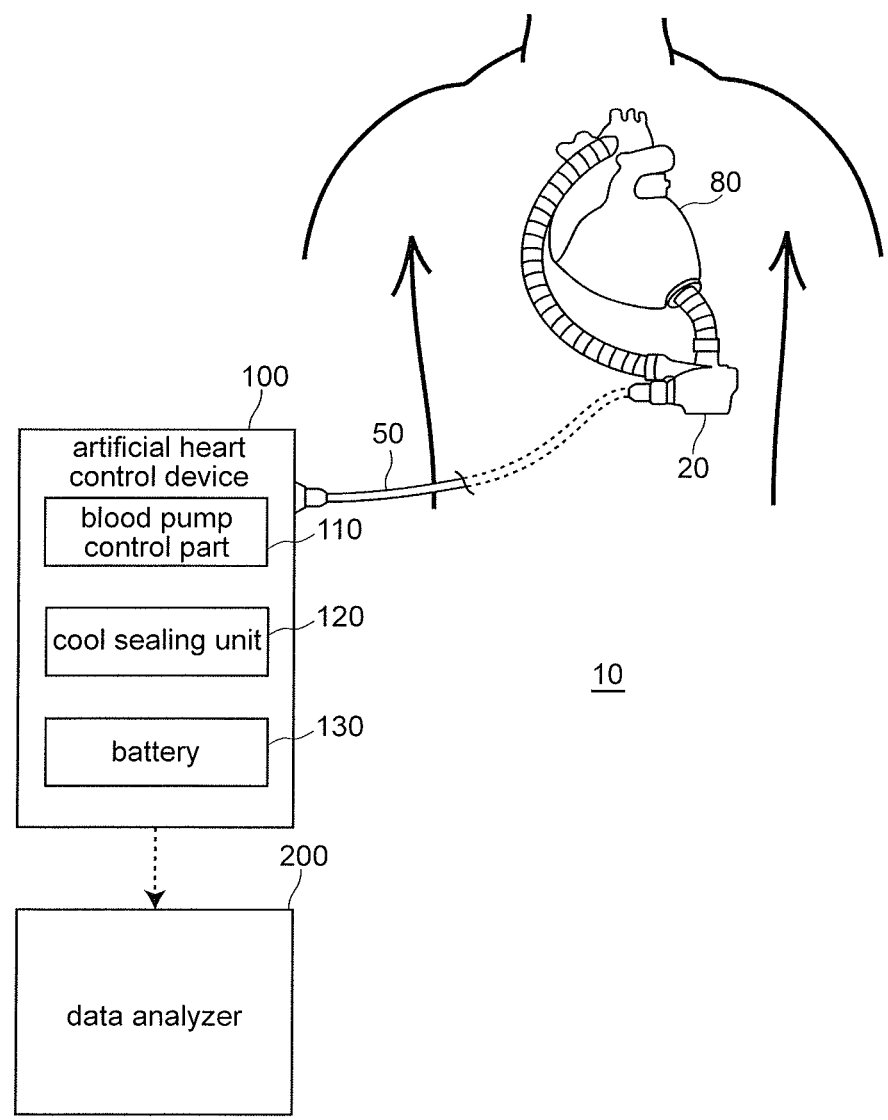
FIG. 1 is a view showing the schematic constitution of an artificial heart device according to one embodiment of the present invention.

FIG. 1 shows the schematic constitution of an artificial heart device according to one embodiment of the present invention.

The artificial heart device (an artificial heart system, a pump system, a motor system in broad meaning) 10 according to this embodiment includes a blood pump (a pump, a motor, an artificial heart pump) 20 and an artificial heart control device (an artificial heart controller) 100. The artificial heart device 10 may further include a data analyzer 200 and one or a plurality of sensors not shown in the drawing. The blood pump 20 and the artificial heart control device 100 are connected with each other by way of a cable 50. The respective sensors are provided for detecting a state of a patient (human body), an operation state of the blood pump 20 or an operation state of respective parts of the artificial heart control device 100 when the blood pump 20 is being operated. For example, the sensor is embedded in a patient's body, is adhered to a patient's body surface or a surface of a patient's organ, is mounted on the blood pump 20, or is installed in the artificial heart control device 100. Detection signals corresponding to detection results of the respective sensors are transmitted to the artificial heart control device 100 via a wired transmission medium or a wireless transmission medium.

The blood pump 20 functions as a left ventricular assist device (LVAD) which assists a function of a left ventricle of a patient's heart 80. The blood pump 20 is a continuous-flow-type blood pump where the flow of blood to be circulated is a continuous flow.

In this embodiment, the blood pump 20 is embedded in the patient's body, and the artificial heart control device 100 is arranged outside the patient's body. However, some of or all functional parts of the artificial heart control device 100 (for example, blood pump 20) may be mounted in the patient's body. The artificial heart control device 100 includes a blood pump control part 110, a cool sealing unit 120 and a detachable battery (a power source in broad meaning) 130. The blood pump control part 110 generates, in a state where a power source voltage is applied to the blood pump control part 110 from the battery 130, a drive current (a drive signal in broad meaning) for driving the blood pump 20 in response to a detection signal transmitted from a sensor not shown in the drawing thus controlling a rotational speed of the blood pump 20. The cool sealing unit 120 circulates lubrication fluid for the blood pump 20. The cable 50 is constituted of a lubrication-fluid-feed-side pipe and a lubrication-fluid-return-side pipe and forms a circulation passage for the lubrication fluid. Further, the cable 50 includes, as a communication cable, a signal line through which a drive current to be supplied to the blood pump 20 from the artificial heart control device 100 is transmitted. The battery 130 includes a built-in battery and an emergency battery, and a power source voltage from either one of the built-in battery and the emergency battery is supplied to respective parts of the artificial heart control device 100 through a power source line. A power source which supplies electric power to the artificial heart control device 100 is not limited to the battery 130, and DC power may be supplied to the artificial heart control device 100 from a commercial power source through an AC-DC adapter.

The data analyzer 200 is configured to be connectable with the artificial heart control device 100 by way of a wired transmission medium or a wireless transmission medium. The artificial heart control device 100 processes operation data or the like corresponding to states of respective parts such as the blood pump 20 and efficiently accumulates such data while reducing data size to be stored. Here, the operation data or the like includes control data for instructing operations of the respective parts such as the blood pump 20 which is an object to be controlled by the artificial heart control device 100, operation data indicative of operation states of the respective parts such as the blood pump 20 which is controlled based on the control data, and biological data indicative of a state of a patient. The data analyzer 200 acquires data accumulated in the artificial heart control device 100 through the transmission medium and executes the processing for analyzing data. The data analyzer 200 can form an image in the form of a graph or a table based on data transmitted from the artificial heart control device 100 or data after data analysis processing transmitted from the artificial heart control device 100, and can display the image on a display part. These functions of the data analyzer 200 can be realized using a personal computer, a dedicated hardware device or the like.

Due to the above-mentioned constitution, even after a patient leads a normal life with the blood pump 20 embedded in his body for a long period, the maintenance of the artificial heart device 10 becomes easy and hence, when an abnormality is detected in the blood pump 20 or the artificial heart control device 100, an operation of the blood pump 20 or the artificial heart control device 100 can be easily inspected.

[Blood Pump]

Figure 2:
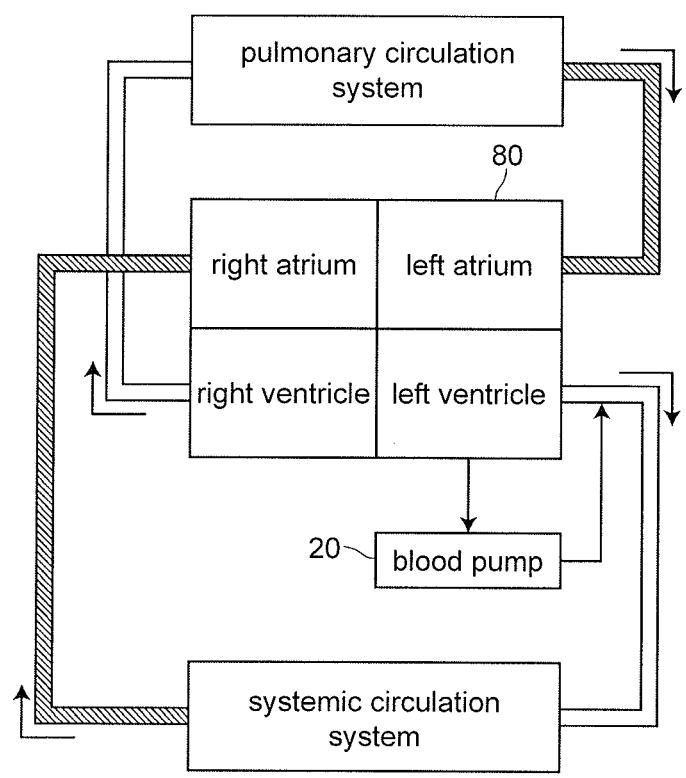
FIG. 2 is an explanatory view of a blood pump according to the embodiment of the present invention.

FIG. 2 is an explanatory view of the blood pump 20 according to this embodiment. FIG. 2 schematically shows the patient's heart 80 and a circulation system in the body.

The heart 80 is partitioned into a left atrium, a left ventricle, a right atrium and a right ventricle. The right atrium and the right ventricle have a function of circulating blood through a pulmonary circulation system, and the left atrium and the left ventricle have a function of circulating blood through a systemic circulation system. That is, the blood which is returned to the heart from the systemic circulation system through a superior vena cava and an inferior vena cava is stored in the right atrium and, thereafter, is sent to the right ventricle. The blood which is sent to the right ventricle circulates through the pulmonary circulation system through a pulmonary trunk by the beating of the right ventricle, and is brought into a state where the blood contains oxygen. The blood which is returned to the heart from the pulmonary circulation system through pulmonary veins is stored in the left atrium and, thereafter, is sent to the left ventricle. The blood which is sent to the left ventricle circulates through the systemic circulation system through a main artery by the beating of the left ventricle. The blood pump 20 according to this embodiment, for assisting the function of the left ventricle, sucks the blood which is sent to the left ventricle, and sends out the blood to the main artery.

Figure 3:
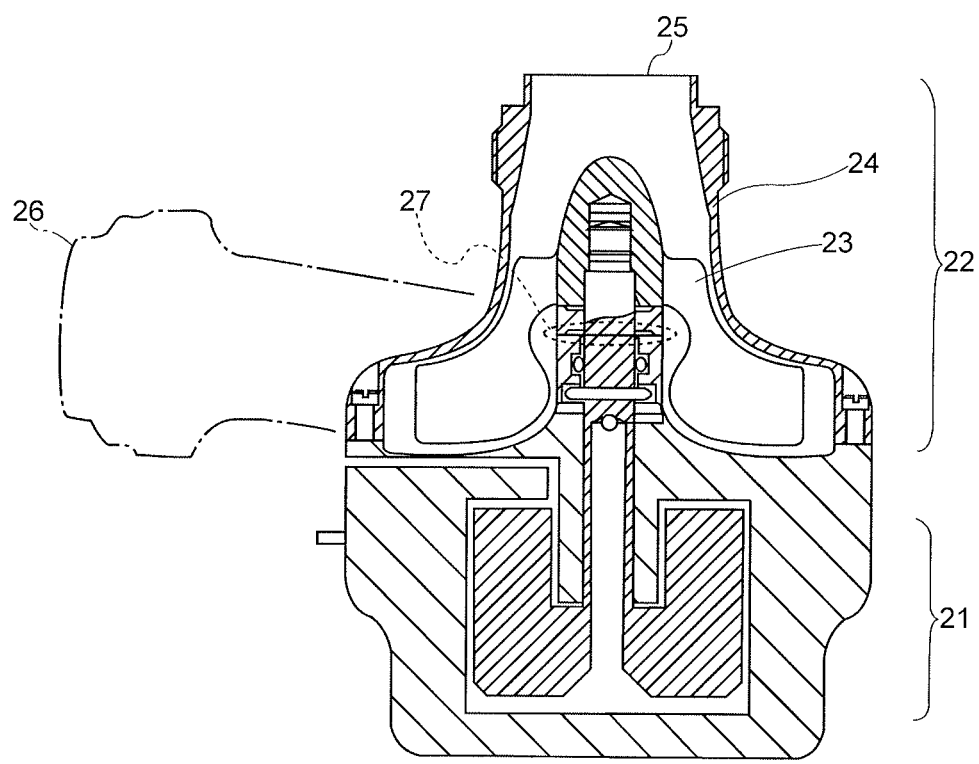
FIG. 3 is a view showing one example of a cross section of the blood pump according to the embodiment of the present invention.

FIG. 3 shows one example of a cross section of the blood pump 20 according to this embodiment. Although FIG. 3 shows a constitutional example of a cross section of the blood pump 20, this embodiment is not limited to the blood pump having the constitution shown in FIG. 3.

The blood pump 20 includes a drive part 21 which has a cylindrical motor and a pump part 22 which is connected to the drive part 21. The pump part 22 includes an impeller 23 which is driven by way of a rotary shaft of the motor, and a pump casing 24 which is connected to the drive part 21 in a state where the pump casing 24 covers the impeller 23. The blood pump 20 is configured such that when blood in a left ventricle of the heart 80 flows into the pump casing 24 via a blood vessel (artificial blood vessel) and an inflow port 25, the impeller 23 imparts flow energy to the blood so that the blood flows out to a main artery. Here, the blood flows out to the main artery via an outflow port 26 formed in a side surface of the pump casing 24 and a blood vessel (artificial blood vessel).

Further, in the blood pump 20, a mechanical seal part 27 is arranged between the drive part 21 and the pump part 22. Accordingly, the pump part 22 and the drive part 21 are slidably and tightly sealed from each other thus considerably effectively suppressing leaking of the blood from the pump part 22 to the drive part 21. As a result, the formation of a blood clot is suppressed thus suppressing stopping of an operation of the pump and a change in an operational state of the pump. The pump part 22 is a centrifugal pump by which a larger blood flow rate can be expected than an axial flow pump, wherein a DC motor can be used as a motor for driving the impeller 23.

[Cool Sealing Unit]

Figure 4:
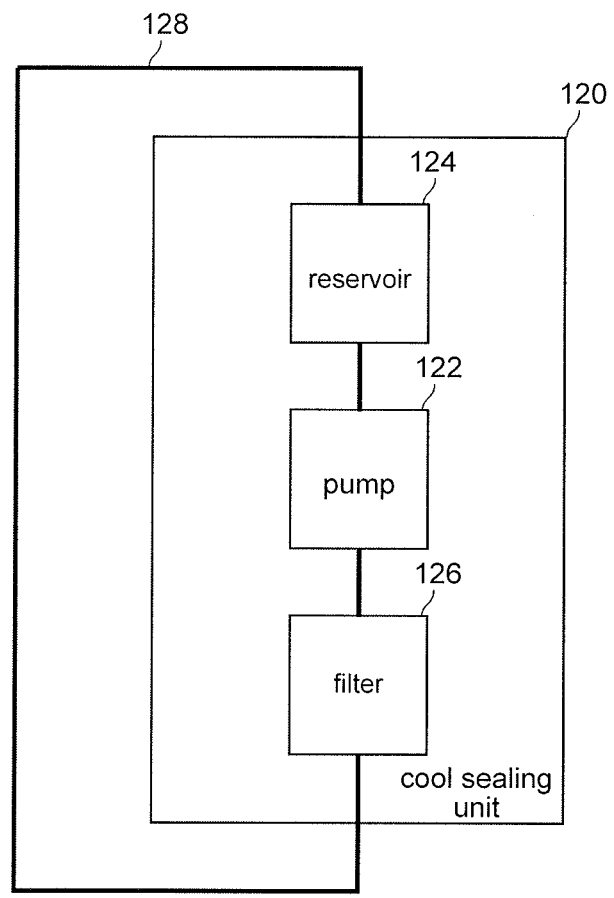
FIG. 4 is a block diagram showing the constitutional example of a cool sealing unit according to the embodiment of the present invention.

FIG. 4 is a block diagram showing the constitutional example of the cool sealing unit 120 according to this embodiment. FIG. 4 schematically shows the overall constitution of the cool sealing unit 120.

The cool sealing unit 120 includes a pump 122, a reservoir 124 and a filter 126. The reservoir 124 reserves cool sealing liquid which is used as lubrication fluid for a bearing portion of the pump part 22 shown in FIG. 3. The cool sealing liquid which is reserved in the reservoir 124 is fed to a circulation passage 128 by the pump 122. The filter 126 is arranged in the circulation passage 128 so as to remove impurities in the cool sealing liquid. The cool sealing unit 120 suppresses the coagulation of blood in the mechanical sealing part 27 and the generation of heat in the drive part 21 and the pump part 22 by circulating cool sealing liquid in the passage which passes the bearing portion of the pump part 22. The cool sealing unit 120 circulates cool sealing liquid by an open loop control in a manner that the cool sealing unit 120 is operated in accordance with an instruction value given from a patient or the like.

[Artificial Heart Control Device and Data Analyzer]

Figure 5:
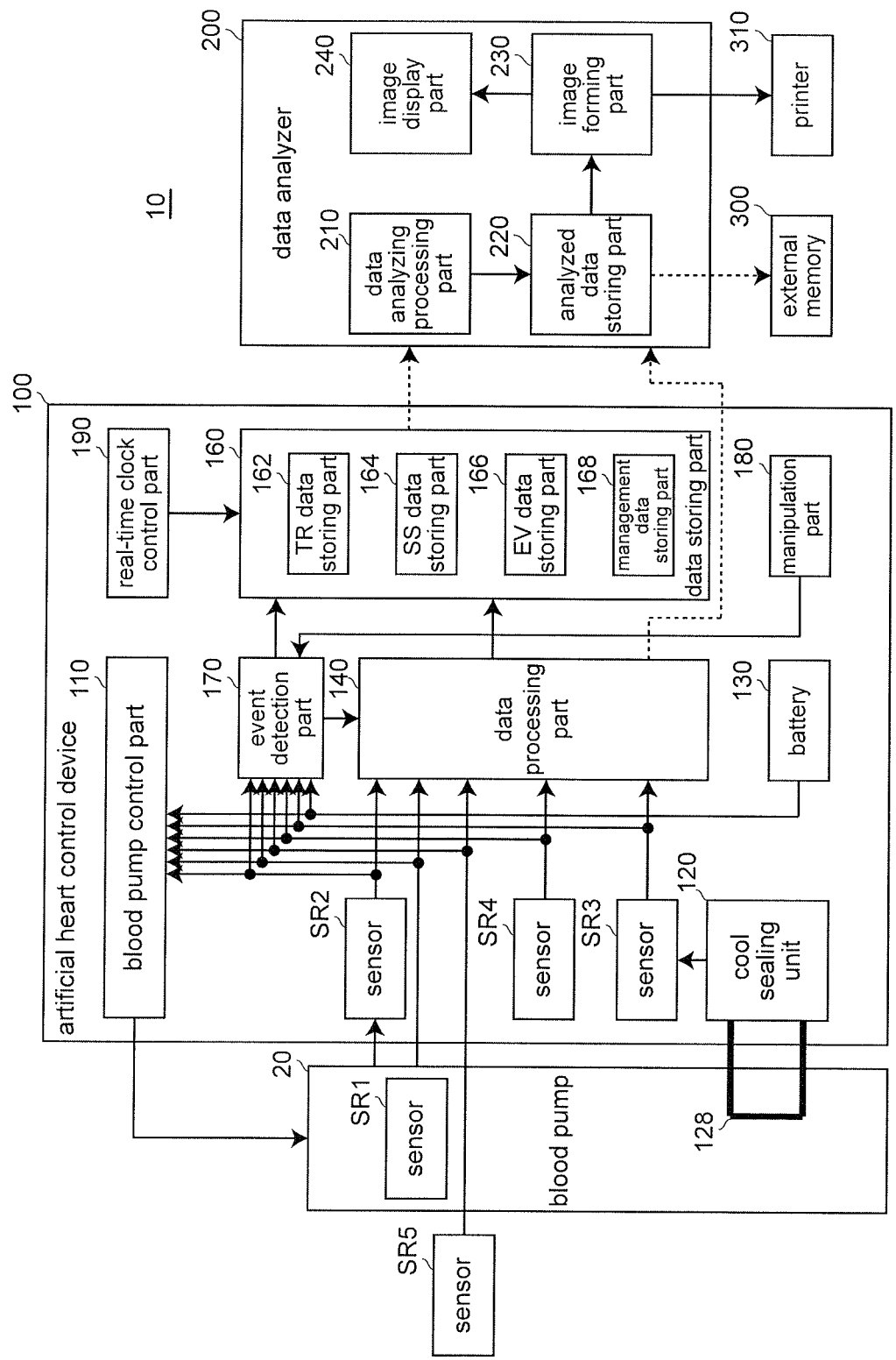
FIG. 5 is a functional block diagram of respective parts of the artificial heart device according to the embodiment of the present invention.

FIG. 5 is a block diagram showing one example of functions of the respective parts of the artificial heart device 10 according to this embodiment. In FIG. 5, parts identical with the parts in FIG. 1 are given the same symbols and their repeated explanation is omitted when appropriate.

The artificial heart device 10 includes one or a plurality of sensors corresponding to objects to be detected in the blood pump 20 or the artificial heart control device 100. To be more specific, the artificial heart device 10 (or the artificial heart control device 100) includes one or a plurality of sensors for acquiring biological data, operation data on the blood pump 20, operation data on the cool sealing unit 120, and/or operation data on the battery 130 which supplies electric power to the artificial heart device 10. Further, the artificial heart control device 100 controls the flow of blood by controlling the blood pump 20 in response to detection signals transmitted from the sensors.

As such a sensor, for example, in FIG. 5, a sensor SR1 is mounted on the blood pump 20 for detecting an operation state of the blood pump 20. Further, in addition to the sensor SR1, a sensor SR2 for detecting an operation state of the blood pump 20 and a sensor SR3 for detecting an operation state of the cool sealing unit 120 are mounted on the artificial heart control device 100. Further, a sensor SR4 for detecting an impact which is applied to the artificial heart control device 100 per se is mounted on the artificial heart control device 100. Still further, the artificial heart control device 100 can fetch a detection signal of a sensor SR5 which is mounted in a patient's body. The sensors SR1 to SR5 respectively include one or a plurality of sensor devices (for example, sensor elements or measuring devices) corresponding to objects to be detected.

Further, the artificial heart control device 100 stores data corresponding to the detection signals transmitted from the sensors SR1 to SR5 after processing the data into one or plural kinds of data. Such an artificial heart control device 100 includes a data processing part 140, a data storing part 160, an event detection part 170, a manipulation part 180 and a real-time clock control part 190 in addition to the blood pump control part 110, the cool sealing unit 120 and the battery 130.

The blood pump control part 110 controls a rotational speed of the blood pump 20 based on at least one of detection signals transmitted from the sensors SR1 to SR5, the battery 130 and the like and manipulation data transmitted from the manipulation part 180. The cool sealing unit 120 circulates cool sealing liquid in the circulation passage 128 in such a manner that the cool sealing unit 120 is operated with a flow passage pressure corresponding to a predetermined instruction value.

The data processing part 140 processes operation data corresponding to detection signals transmitted from the sensors SR1 to SR5, biological data and operation data corresponding to an operation state of the battery 130 (operation data on a power source which supplies electric power to the artificial heart device 10 in broad meaning). The data processing part 140 outputs processed data: such data processing varies depending on how the data will be used after being stored.

The data processing part 140 performs first data processing on operation data corresponding to detection signals transmitted from the sensors SR1 to SR5, biological data and operation data corresponding to an operation state of the battery 130. In the first data processing, data processing is performed on the above-mentioned operation data or biological data in a first period (for example, 10 minutes). Data after the first data processing is stored as trend data (hereinafter, referred to as TR data) in association with date-and-time data.

Further, the data processing part 140 performs second data processing on operation data corresponding to detection signals transmitted from the sensors SR1 to SR5, biological data, operation data corresponding to an operation state of the battery 130 and manipulation data transmitted from the manipulation part 180. In the second data processing, data processing is performed on operation data, biological data and manipulation data in a second period (for example, 5 seconds) before and after predetermined event detection timing. The second period is preferably set shorter than the first period. Data after the second data processing is stored as snapshot data (hereinafter, referred to as SS data) in association with date-and-time data.

Further, the data processing part 140 directly outputs operation data corresponding to instantaneous values of detection signals transmitted from the sensors SR1 to SR5, biological data, and operation data corresponding to an instantaneous value indicative of an operation state of the battery 130 substantially with no processing. That is, the data processing part 140 performs such simple processing as noise removal processing, for example, and outputs the above-mentioned data as real-time data (hereinafter, referred to as RT data).

The event detection part 170 detects the occurrence and end of an event which agrees with any one of a plurality of preset event conditions. To be more specific, the event detection part 170 detects the occurrence and end of an event based on at least one of operation data, biological data, mounting and removal data which is updated at the time of mounting or removing the battery 130 and manipulation data. The operation data includes operation data corresponding to detection signals transmitted from the sensors SR1 to SR5 and operation data corresponding to an operation state of the battery 130. The biological data is data corresponding to a detection signal transmitted from the sensor SR5. The mounting and removal data is updated based on a detection signal transmitted from the battery 130 at the time of mounting or removing the battery 130. The manipulation data is data corresponding to manipulation contents of the manipulation part 180. The data processing part 140 generates SS data in the second period ranging from a point of time before timing at which the occurrence of an event is detected by the event detection part 170 to a point of time after such timing. Here, the event detection part 170 generates event data (hereinafter, referred to as EV data) corresponding to a detected event.

The data storing part 160 includes a TR data storing part (first data storing part) 162, an SS data storing part (second data storing part) 164, an EV data storing part (third data storing part) 166, and a management data storing part (fourth data storing part) 168.

The TR data storing part 162 stores TR data transmitted from the data processing part 140. To be more specific, each time the first period elapses, TR data which is processed by the data processing part 140 is stored in the TR data storing part 162 in association with date-and-time data corresponding to date and time at which TR data is stored. The TR data storing part 162 is configured such that stored data is retrievable from the TR data storing part 162.

The SS data storing part 164 stores SS data transmitted from the data processing part 140. To be more specific, SS data is stored in the SS data storing part 164 in association with date-and-time data corresponding to date and time at which SS data is stored. The SS data storing part 164 is configured such that stored data is retrievable from the SS data storing part 164.

The EV data storing part 166 stores EV data transmitted from the event detection part 170. To be more specific, EV data generated by the event detection part 170 is stored in the EV data storing part 166 in association with date-and-time data corresponding to date and time at which EV data is stored. The EV data storing part 166 is configured such that stored data is retrievable from the EV data storing part 166.

In the management data storing part 168, at least one of information on a patient in which the blood pump 20 is mounted, identification numbers which are given to constitutional elements of the artificial heart device 10, the time the artificial heart device 10 was used, an identification number which is given to the battery 130 (a power source in broad meaning), the time the battery 130 was used, and the number of times of charge to the battery 130 is stored. As the above-mentioned information on a patient, for example, a patient ID which is allocated to each patient, name, sex, age, height, weight and the like of the patient are named. As the identification number allocated to the constitutional element of the artificial heart device 10, for example, the identification number allocated to the blood pump 20 or the artificial heart control device 100 is named. Further, the management data storing part 168 may store not only the identification number of the blood pump 20 or the artificial heart control device 100 but also the identification numbers of other constitutional elements. The time the artificial heart device 10 was used or the time the battery 130 was used is measured by a dedicated circuit, for example. Also the number of times of charge to the battery 130 is measured by a dedicated circuit in the same manner, for example. The management data storing part 168 is configured such that respective stored data are retrievable from the management data storing part 168.

The manipulation part 180 is provided for allowing a patient himself, a doctor or the like to control the artificial heart device 10, and is constituted of any one of manipulation means including a manipulation button, a remote controller, a mouse, a touch pad, a switch and the like. Further, a microphone for voice inputting may be also adopted as the manipulation part 180. Control data for controlling the artificial heart device 10 is generated based on manipulation data on the manipulation part 180, and the respective parts of the artificial heart control device 100 are controlled based on the control data.

The real-time clock control part 190 generates date-and-time data which is constituted of "year", "month", "date", "hour", "minute" and "second" corresponding to a present time. The date-and-time data is supplied to the data storing part 160.

As described above, data which is stored in the artificial heart control device 100 is retrieved by the data analyzer 200 which is connected to the artificial heart control device 100 through a communication cable which is a known transmission medium or the like when a patient is subjected to a periodic medical checkup. Accordingly, the data analyzer 200 can later analyze an operation state of the artificial heart control device 100, the blood pump 20 or the like in the artificial heart device 10 which is operated for a long period.

In conjunction with FIG. 5, the explanation has been made with respect to the example where the data processing part 140 and the data storing part 160 are incorporated in the artificial heart control device 100. However, at least one of the data processing part 140 and the data storing part 160 may be provided separately from the blood pump control part 110. For example, the blood pump 20 may have the functions of the sensors SR2 to SR4, the function of the data processing part 140, and the function of the data storing part 160.

The data analyzer 200 acquires TR data, SS data and EV data which are stored in the data storing part 160 as described above. Further, the data analyzer 200 can receive RT data which is generated by the artificial heart control device 100 virtually in real time through the above-mentioned communication cable.

The data analyzer 200 having such a constitution includes a data analyzing processing part 210, an analyzed data storing part 220, an image forming part 230 and an image display part 240.

The data analyzing processing part 210 performs data analyzing processing such as format conversion processing of acquired date-and-time data and respective data corresponding to the date-and-time data on data transmitted from the artificial heart control device 100. Data after processing performed by the data analyzing processing part 210 is stored in the analyzed data storing part 220 as analyzed data. Further, RT data transmitted from the artificial heart control device 100 is temporarily stored in the analyzed data storing part 220, for example. The image forming part 230 generates image data corresponding to an image such as a graph or a table based on the data stored in the analyzed data storing part 220. The image display part 240 is constituted of a known display device such as a liquid crystal display and an organic EL (Electro Luminescence) display, and displays an image based on image data generated by the image forming part 230.

The data analyzer 200 is configured such that an external memory 300 which is a portable auxiliary storage device can be connected to the data analyzer 200. Accordingly, data stored in the analyzed data storing part 220 can be transferred to the external memory 300, for example. Accordingly, processing which uses data after analyzing processing can be performed by a device different from the data analyzer 200. Further, data on an image formed by the image forming part 230 may be transferred to the external memory 300. Further, the data analyzer 200 is configured such that a printer 310 can be connected to the data analyzer 200 so that an image formed by the image forming part 230 can be printed by the printer 310.

Figure 6:
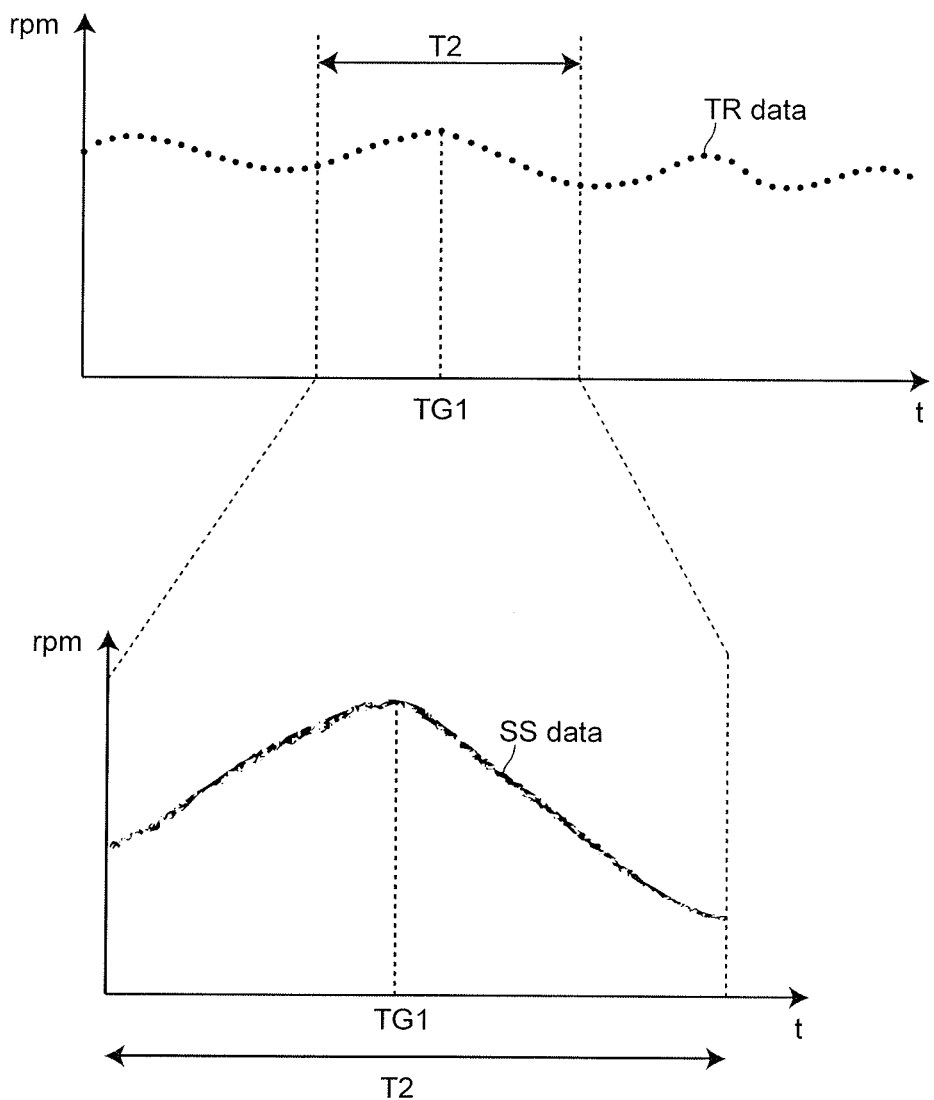
FIG. 6 is an explanatory view of TR data and SS data according to the embodiment of the present invention.

FIG. 6 is an explanatory view of TR data and SS data according to this embodiment. TR data and SS data according to this embodiment are explained in conjunction with a case shown in FIG. 6 where time is taken on an axis of abscissas, and data corresponding to a rotational speed of the blood pump 20 which is generated based on a detection signal transmitted from the sensor SR1 is taken on an axis of ordinates. The same goes for TR data and SS data which are generated based on other detection signals in this embodiment.

In the TR data storing part 162, TR data is stored each time the first period T1 (for example, 10 minutes) elapses. Accordingly, compared to a case where an instantaneous value of a detection signal transmitted from the sensor is sequentially accumulated, it is possible to reduce storage capacity. Although a change in rotational speed of the blood pump 20 over a long period can be found using such TR data, it is difficult to understand a change in rotational speed of the blood pump 20 within a relatively short period using such TR data.

The event detection part 170 detects the presence or non-presence of the occurrence of an event based on a detection signal transmitted from the sensor or the like. When the occurrence of the event is detected by the event detection part 170, SS data in a second period T2 (for example, 5 seconds) ranging from a point of time before event detection timing TG1 to a point of time after the event detection timing TG1 is stored in the SS data storing part 164. Accordingly, it is unnecessary to uselessly sequentially accumulate operation data in a storing part 164, and it is sufficient to merely accumulate detailed data only on minimum required portions. Accordingly, the data analyzer 200 can analyze an event occurrence state in detail by analyzing SS data. By analyzing SS data, it becomes possible to understand a change in rotational speed of the blood pump 20 within a short period before and after the occurrence of the event which particularly requires the analysis and hence, it is possible to understand the movement of the blood pump 20 within a short period which cannot be analyzed using only TR data.

Hereinafter, the artificial heart device 10 according to this embodiment is explained specifically.

[Example of Stored Data]

Figure 7:
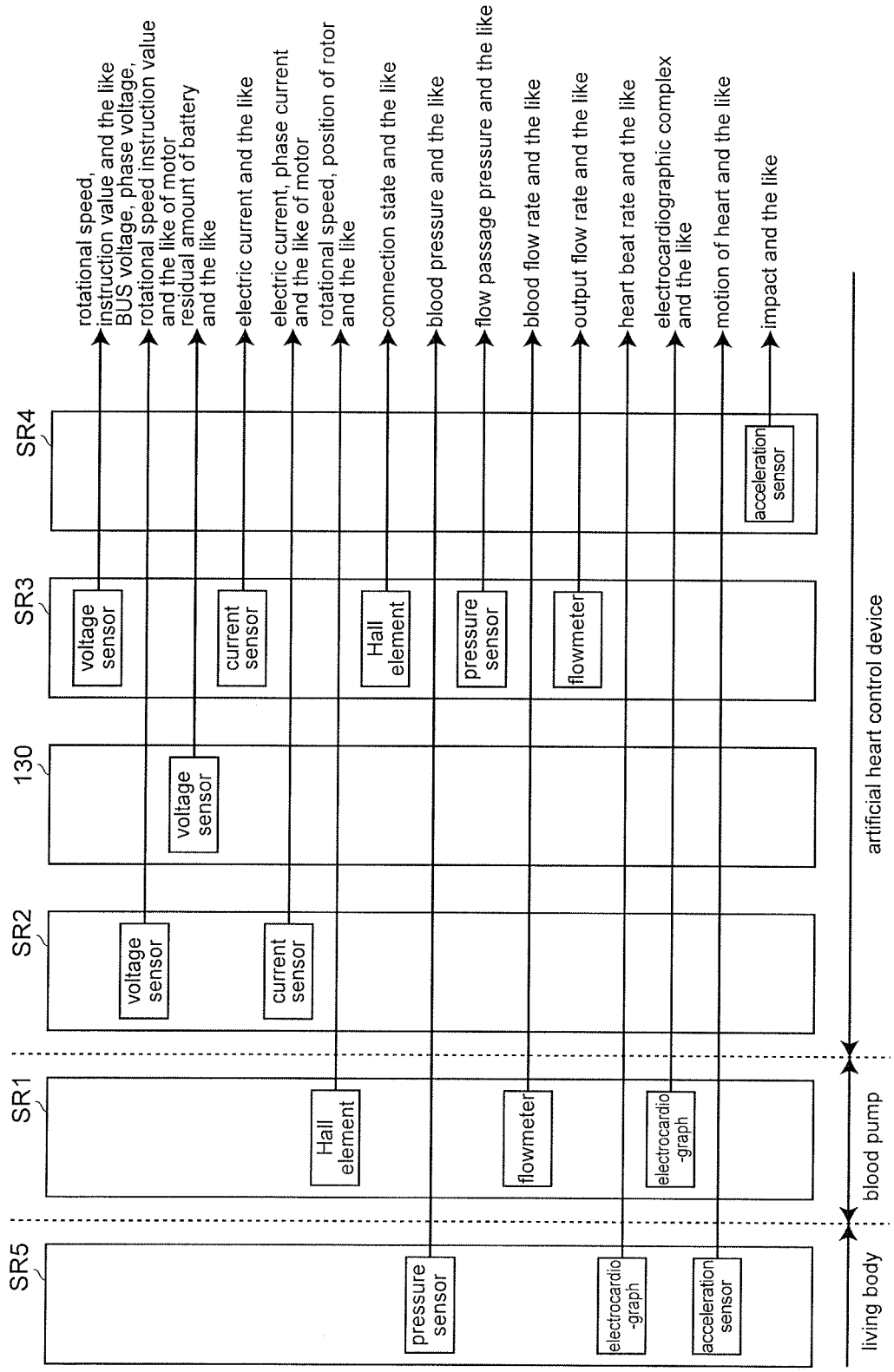
FIG. 7 is an explanatory view of data which is an object to be stored in the artificial heart control device according to the embodiment of the present invention.

FIG. 7 is an explanatory view of data to be stored in the artificial heart control device 100 according to this embodiment. FIG. 7 shows the relationship between the sensors which are mounted on respective parts of the artificial heart device 10 and the patient's body and the data to be stored. Here, in FIG. 7, parts identical with the parts shown in FIG. 5 are given same symbols and their repeated explanation is omitted when appropriate.

The sensor SR1 is constituted of sensor devices such as a Hall element, a flowmeter and an electrocardiograph, and the sensor SR1 detects detection signals corresponding to an operation state of the blood pump 20. To be more specific, the respective sensor devices which constitute the sensor SR1 generate detection signals corresponding to a rotational speed of the blood pump 20, a position of the rotor which constitutes the blood pump 20, a blood flow rate of the blood pump 20 and an electrocardiographic complex. The artificial heart control device 100 controls the blood pump 20 and the like using these detection signals and, at the same time, processes data generated based on the detection signals as operation data corresponding to an operation state of the blood pump 20 and stores the operation data.

The sensor SR2 is constituted of sensor devices such as a voltage sensor and a current sensor, and detects detection signals corresponding to an operation state of the blood pump 20. To be more specific, the respective sensor devices which constitute the sensor SR2 generate detection signals corresponding to a BUS voltage, a phase voltage, rotational speed instruction value and the like of a motor of the blood pump 20. The artificial heart control device 100 controls the blood pump 20 and the like using these detection signals and, at the same time, processes data generated based on the detection signals as operation data corresponding to an operation state of the blood pump 20 and stores the operation data.

The sensor SR3 is constituted of sensor devices such as a voltage sensor, a current sensor, a Hall element, a pressure sensor and a flowmeter, and detects detection signals corresponding to an operation state of the cool sealing unit 120. To be more specific, the respective sensor devices which constitute the sensor SR3 generate detection signals corresponding to a rotational speed instruction value of the motor, an electric current, a connection state, a flow passage pressure, an output flow rate and the like with respect to the cool sealing unit 120. The artificial heart control device 100 processes data generated based on these detection signals as operation data corresponding to an operation state of the cool sealing unit 120, and stores the operation data.

The sensor SR4 is constituted of an acceleration sensor. the acceleration sensor generates a detection signal corresponding to an impact imparted to the artificial heart control device 100. The artificial heart control device 100 processes data generated based on the detection signal as data corresponding to a use state of the artificial heart control device 100 and stores the data.

The sensor SR5 is constituted of sensor devices such as a pressure sensor, an electrocardiograph and an acceleration sensor. The respective sensor devices which constitute the sensor SR5 generate detection signals corresponding to a patient's blood pressure, a patient's heart beat rate, a movement of a patient's heart and the like. Further, the sensor SR5 may be provided with a sensor device which generates a detection signal corresponding to a temperature or a posture of the patient. The artificial heart control device 100 controls the blood pump 20 and the like using the detection signals and, at the same time, processes data generated based on the detection signals as biological data corresponding to a state of the patient and stores the biological data.

The battery 130 includes a voltage sensor, and the voltage sensor generates detection signals corresponding to a residual amount of the battery and a mounting and removal state of the battery. The artificial heart control device 100 processes data generated based on the detection signals as operation data corresponding to an operation state of the battery 130 and stores the operation data. Further, the battery 130 incorporates a dedicated circuit therein, and information corresponding to the number of times of charge is a cumulated in the dedicated circuit. This information is readable and is accumulated in the management data storing part 168.

FIG. 8 shows one example of TR data according to this embodiment. That is, FIG. 8 shows one example of TR data generated using at least one of the sensors SR1 to SR5 shown in FIG. 7.

TR data includes date-and-time data corresponding to date and time at which TR data is stored in the TR data storing part 162, blood pump operation data, cool sealing unit operation data and battery operation data.

Blood pump operation data may include a rotational speed (instruction value) for controlling the blood pump 20, a rotational speed (actually measured value) of the blood pump 20, a maximum value of the rotational speed, a minimum value of the rotational speed, power consumption, a maximum value of power consumption, and a minimum value of power consumption. The rotational speed (instruction value) and the power consumption are calculated or specified based on detection signals transmitted from the sensor SR2, for example. Here, the power consumption is calculated based on a product of an electric current value corresponding to a detection signal and a voltage value corresponding to a detection signal or a given fixed voltage value. The rotational speed (actually measured value) is calculated or specified based on a detection signal transmitted from the sensor SR1, for example. Out of these operation data, a maximum value and a minimum value are calculated by data processing in the data processing part 140.

Cool sealing unit operation data includes a flow passage pressure (instruction value), a rotational speed (actually measured value), a maximum value of the rotational speed, a minimum value of the rotational speed, power consumption, a maximum value of the power consumption, a minimum value of the power consumption, a flow passage pressure (actually measured value), a maximum value of the flow passage pressure, and a minimum value of the flow passage pressure with respect to the cool sealing unit 120. The flow passage pressure (instruction value), the rotational speed (actually measured value), the power consumption and the flow passage pressure (actually measured value) are calculated or specified based on detection signals transmitted from the sensor SR3, for example. Out of these operation data, the maximum value and the minimum value are calculated by data processing in the data processing part 140.

Battery operation data includes an operation voltage of the battery 130. The operation voltage is determined by a voltage sensor mounted on the battery 130, for example.

In this embodiment, respective data shown in FIG. 8 are generated for every 10 minutes and generated data are stored in the TR data storing part 162. That is, to reduce a size of data, in place of simply sampling operation data or the like for every 10 minutes, just data after data processing is stored in the TR data storing part 162 as representative data representing an operation during 10 minutes.

Here, TR data in this embodiment is not limited to data shown in FIG. 8 and may include biological data corresponding to a state of a patient who mounts the blood pump 20 on his body, and data corresponding to a use state of the artificial heart control device 100 corresponding to a detection signal transmitted from the sensor SR4.

FIG. 9 shows one example of SS data according to this embodiment. FIG. 9 shows one example of SS data generated using at least one of the sensors SR1 to SR5 shown in FIG. 7.

SS data includes date-and-time data corresponding to date and time at which SS data is stored in the SS data storing part 164, blood pump operation data, cool sealing unit operation data, battery operation data, and a state of an event.

Blood pump operation data may include a rotational speed and power consumption of the blood pump 20. The power consumption is calculated or specified based on detection signals transmitted from the sensor SR2, for example. The rotational speed is calculated or specified based on detection signals transmitted from the sensor SR1, for example.

Cool sealing unit operation data includes a flow passage pressure, a rotational speed and power consumption of the cool sealing unit 120. The flow passage pressure, the rotational speed and the power consumption are calculated or specified based on detection signals transmitted from the sensor SR3, for example.

Battery operation data includes an operation voltage of the battery 130. The operation voltage is specified by a voltage sensor which is mounted on the battery 130, for example.

A state of an event is data corresponding to an event which is detected by the event detection part 170.

In this embodiment, during 5 seconds ranging from a point of time before timing at which the event detection part 170 detects an event to a point of time after timing at which the event detection part 170 detects the event, the respective data shown in FIG. 9 are generated and are stored in the SS data storing part 164. Accordingly, when the operation of the artificial heart device cannot be analyzed using only TR data, it is sufficient to merely accumulate detailed data only on minimum required portions. Here, by analyzing such SS data by the data analyzer 200, a state of the occurrence of an event can be analyzed in detail.

SS data used in this embodiment is not limited to data shown in FIG. 9 and may include biological data corresponding to a state of the patient who mounts the blood pump 20 on his body or data corresponding to a use state of the artificial heart control device 100 in response to a detection signal transmitted from the sensor SR4.

FIG. 10 shows one example of EV data according to this embodiment. FIG. 10 shows one example of EV data which is generated using at least one of the sensors SR1 to SR5 shown in FIG. 7.

EV data are data each of which indicates an occurrence state of an event which is detected when the event agrees with an event detection condition preset by the event detection part 170. EV data includes data on a battery mounting and removal event, data on a blood pump rotational speed detection event, and data on a blood pump power consumption detection event. Further, EV data includes data on a cool-sealing-unit rotational speed detection event, data on a cool-sealing-unit power consumption detection event, data on a cool-sealing-unit flow passage pressure detection event, and data on a cool-sealing-unit disconnection detection event. Still further, EV data may include data on a blood pump start event, data on a blood pump stop event, and data on a manipulation event.

The event detection part 170 detects the beginning and ending of the above-mentioned event in response to a detection signal transmitted from at least one of sensors SR1 to SR5 shown in FIG. 7.

The data on the battery mounting and removal event is updated at the time of mounting or removing the battery 130, and includes information such as date and time at which the battery 130 is mounted and date and time at which the battery 130 is removed. The battery mounting and removal event is detected based on a detection signal transmitted from the voltage sensor which is mounted on the battery 130 or operation data which is generated corresponding to the detection signal, for example.

The blood pump rotational speed detection event is detected as abnormality in rotational speed when the blood pump 20 is operated in a state where a rotational speed of the blood pump 20 does not fall within a predetermined range of rotational speed. The blood pump power consumption detection event is detected as abnormality in power consumption when the blood pump 20 is operated in a state where power consumption of the blood pump 20 does not fall within a predetermined range of power consumption. These events are detected based on detection signals transmitted from the sensors SR1, SR2 or operation data generated corresponding to the detection signals, for example.

The cool-sealing-unit rotational speed detection event is detected as abnormality in rotational speed when the cool sealing unit 120 is operated in a state where a rotational speed of the cool sealing unit 120 does not fall within a predetermined range of rotational speed. The cool-sealing-unit power consumption detection event is detected as abnormality in power consumption when the cool sealing unit 120 is operated in a state where the power consumption of the cool sealing unit 120 does not fall within a predetermined range of power consumption. The cool-sealing-unit flow passage pressure detection event is detected as abnormality in flow passage pressure when a flow passage pressure in a circulation passage for lubrication fluid does not fall within a predetermined range of pressure. The cool-sealing-unit disconnection detection event is an event where a disconnection state of a signal line for controlling of a circulation passage for lubrication fluid or the cool sealing unit 120 is detected as abnormality in disconnection. These events are detected based on detection signals transmitted from the sensor SR3 or operation data which are generated corresponding to the detection signals, for example.

The blood pump start event includes information such as date and time at which the blood pump 20 is started. The blood pump stop event includes information such as date and time at which the blood pump 20 is stopped. The manipulation event is an event based on which it is determined whether or not a manipulation corresponding to a predetermined event detection condition is performed by the manipulation part 180. These events are detected based on detection signals transmitted from the sensors SR1, SR3, operation data which are generated corresponding to the detection signals or manipulation data generated by the manipulation part 180.

As described above, the event detection part 170 can detect the occurrence of an event and also can detect the end of the event in the same manner. That is, the event detection part 170 detects the event based on at least one of operation data on the blood pump 20, operation data on the cool sealing unit 120, operation data on the battery 130, mounting and removal data on the battery 130, and manipulation data on the manipulation part 180. In this embodiment, every time an event is detected by the event detection part 170, out of the data, the data corresponding to the event is updated as shown in FIG. 10, and the updated data is stored in the EV data storing part 166. Accordingly, even when the artificial heart device 10 is operated for a long period and an operation state of the artificial heart device 10 is periodically analyzed, it is possible to understand an event occurrence state by referencing EV data.

EV data according to this embodiment is not limited to data shown in FIG. 10. For example, an event occurrence state which is detected based on biological data corresponding to a state of a patient who mounts the blood pump 20 on his body or data corresponding to a use state of the artificial heart control device 100 corresponding to detection signals transmitted from the sensor SR4 may be stored as EV data, for example.

FIG. 11 shows one example of RT data according to this embodiment. FIG. 11 shows one example of RT data which is generated using at least one of sensors SR1 to SR5 shown in FIG. 7.

RT data is data where an instantaneous value of each detection signal is directly outputted from each sensor without being stored in the data storing part 160. RT data includes blood pump operation data, cool sealing unit operation data, battery operation data and an event state.

Blood pump operation data may include a rotational speed (instruction value) for controlling the blood pump 20, a rotational speed (actually measured value) and power consumption of the blood pump 20. The rotational speed (instruction value) and the power consumption are calculated or specified based on detection signals transmitted from the sensor SR2, for example. The rotational speed (actually measured value) is calculated or specified based on a detection signal transmitted from the sensor SR1, for example.

The cool sealing unit operation data includes a flow passage pressure (instruction value), a rotational speed (actually measured value), power consumption, and a flow passage pressure (actually measured value) of the cool sealing unit 120. The flow passage pressure (instruction value), the rotational speed (actually measured value), the power consumption, and the flow passage pressure (actually measured value) are calculated or specified based on detection signals transmitted from the sensor SR3, for example.

Battery operation data includes an operation voltage of the battery 130. The operation voltage is specified by a voltage sensor which is mounted on the battery 130, for example.

The event state is data corresponding to an event which is detected by the event detection part 170.

In this embodiment, respective data shown in FIG. 11 are sequentially generated without being stored in the data storing part 160. By allowing the artificial heart device 10 to directly output RT data generated in this manner without processing, RT data is usefully used for monitoring a present operation state of the artificial heart control device 100 and the blood pump 20.

RT data according to this embodiment is not limited to data shown in FIG. 11 and may include biological data corresponding to a state of a patient who mounts the blood pump 20 on his body or data corresponding to a use state of the artificial heart control device 100 in response to a detection signal transmitted from the sensor SR4. That is, the artificial heart control device 100 (artificial heart device 10) is configured such that the artificial heart control device 100 can output at least one data out of the operation data on the blood pump 20, the operation data on the cool sealing unit 120, the biological data and the operation data on the battery 130. Further, the artificial heart control device 100 may be configured such that the artificial heart control device 100 can output data corresponding to a use state (the degree of impact which the artificial heart control device 100 receives) of the artificial heart control device 100 based on a detection signal transmitted from the sensor SR4.

Figure 12:
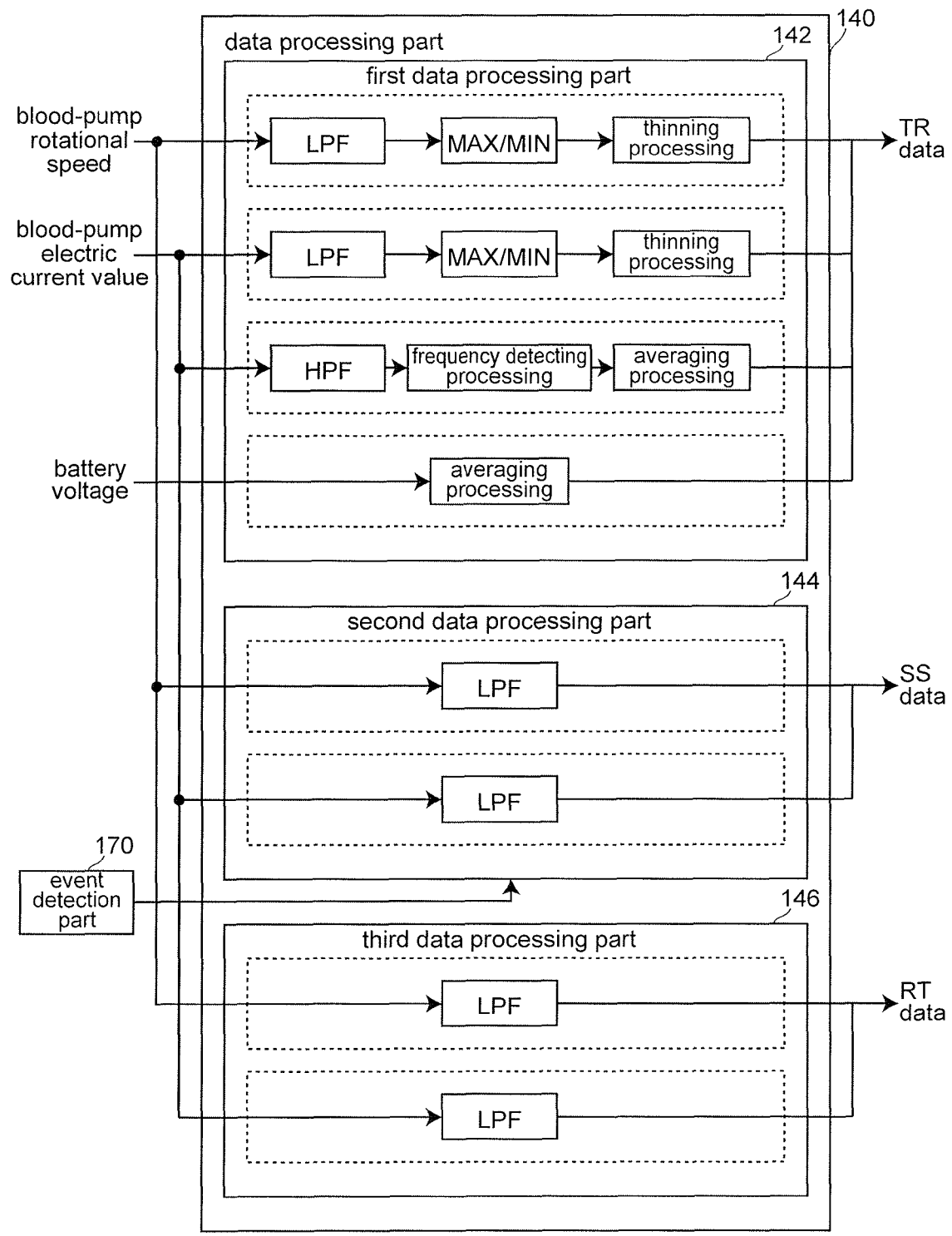
FIG. 12 is a block diagram showing the constitutional example of a data processing part according to the embodiment of the present invention.

FIG. 12 is a block diagram showing a constitutional example of the data processing part 140 according to this embodiment. In FIG. 12, the event detecting part 170 is also shown besides the data processing part 140. FIG. 12 shows an example of data processing which is performed on a blood-pump rotational speed specified by a detection signal transmitted from the sensor SR1, a blood-pump electric current value specified by a detection signal transmitted from the sensor SR2, and a battery voltage detected in the battery 130. However, the substantially same data processing may be applied also to operation data or the like which are specified by other detection signals or the like.

The data processing part 140 includes a first data processing part 142, a second data processing part 144 and a third data processing part 146.

The first data processing part 142 performs first data processing on data corresponding to input signals in a first period. The first data processing desirably includes calculation processing for acquiring an average value by calculation in a first period, calculation processing for acquiring a maximum value by calculation in the first period, calculation processing for acquiring a minimum value by calculation in the first period, and predetermined filter processing.

For example, the first data processing part 142 sequentially performs low pass filter (LPF) processing with cutoff frequency of 50 Hz, maximum value/minimum value filter processing and thinning processing on a detection signal corresponding to a blood-pump rotational speed. Noises are removed by the low pass filter processing. Systole and diastole of a heart can be detected by maximum value/minimum value filter processing. For example, systole and diastole is desirably calculated for every 1 second. Data size of TR data can be reduced by thinning processing.

The first data processing part 142 also sequentially performs low pass filter processing with cutoff frequency of 30 Hz, maximum value/minimum value filter processing and thinning processing on a detection signal corresponding to a blood-pump electric current value, for example. Beat components of a heart can be detected by the low pass filter processing. Also in this case, maximum value/minimum value filter processing and thinning processing can acquire the substantially same advantageous effects as in the case where these processing are performed on the blood-pump rotational speed.

The first data processing part 142 also sequentially performs high pass filter (HPF) processing with cutoff frequency of 2 Hz, frequency detecting processing and averaging processing on the detection signal corresponding to a blood-pump electric current value, for example. A fluctuation in average values of detection signals can be removed by high pass filter processing. A cycle of a heart beat rate can be detected by frequency detecting processing based on a detection signal after the removal of the fluctuation in an average value. The heart beat rate detected by the frequency detecting processing can be averaged by averaging processing.

Further, the first data processing part 142 performs averaging processing on a detection signal corresponding to a battery voltage, for example. Due to such processing, an average value of operational voltages of the battery 130 can be outputted as TR data.

In this manner, data after first data processing corresponding to the detection signal is outputted as TR data.

The second data processing part 144 performs second data processing on data corresponding to input signals. The second data processing desirably includes calculation processing for acquiring an average value by calculation, calculation processing for acquiring a maximum value by calculation, calculation processing for acquiring a minimum value by calculation, and predetermined filter processing. In FIG. 12, second data processing is exemplified as processing which includes filter processing corresponding to a sampling frequency of an input signal (input data) which is an object to be processed.

For example, the second data processing part 144 performs low pass filter processing with cutoff frequency of 10 Hz corresponding to the sampling frequency on a detection signal corresponding to a blood-pump rotational speed, for example. The second data processing part 144 performs low pass filter processing with cutoff frequency of 10 Hz corresponding to the sampling frequency on a detection signal corresponding to a blood-pump electric current value, for example. The second data processing part 144 accumulates just data after second data processing for a period of 5 seconds which is the latest second period. When an event is detected by the event detection part 170, the second data processing part 144 collectively outputs the accumulated data for 5 seconds ranging from a point of time before event detection timing to a point of time after the event detection timing at once. Due to such processing, out of data after second data processing, only data in the second period ranging from the point of time before event detection timing and the point of time after the event detection timing can be outputted as the SS data. The SS data is data which has a short sampling cycle compared to the TR data so that the SS data can display finer changes.

In this manner, data after second data processing corresponding to the detection signal is outputted as SS data.

The third data processing part 146 performs third data processing on data corresponding to input signals. The third data processing desirably includes noise removing processing.

For example, the third data processing part 146 performs low pass filter processing with cutoff frequency of 50 Hz on a detection signal corresponding to a blood-pump rotational speed. Noises are removed by the low pass filter processing. The third data processing part 146 also performs low pass filter processing with cutoff frequency of 40 Hz on a detection signal corresponding to a blood-pump electric current value, for example. Noises are removed by the low pass filter processing.

In this manner, data after third data processing corresponding to the detection signal is outputted as RT data without being stored in the data storing part 160.

Besides the TR data and the SS data which are generated in the above-mentioned manner, the EV data is stored in the data storing part 160 and, thereafter, these data are retrieved by the data analyzer 200 connected to the artificial heart control device 100 through a communication cable or the like. The RT data which is generated in the above-mentioned manner is transmitted to the data analyzer 200 connected to the artificial heart control device 100 through a communication cable or the like.

[Example of Manner of Operation of Data Analyzer]

Figure 13:
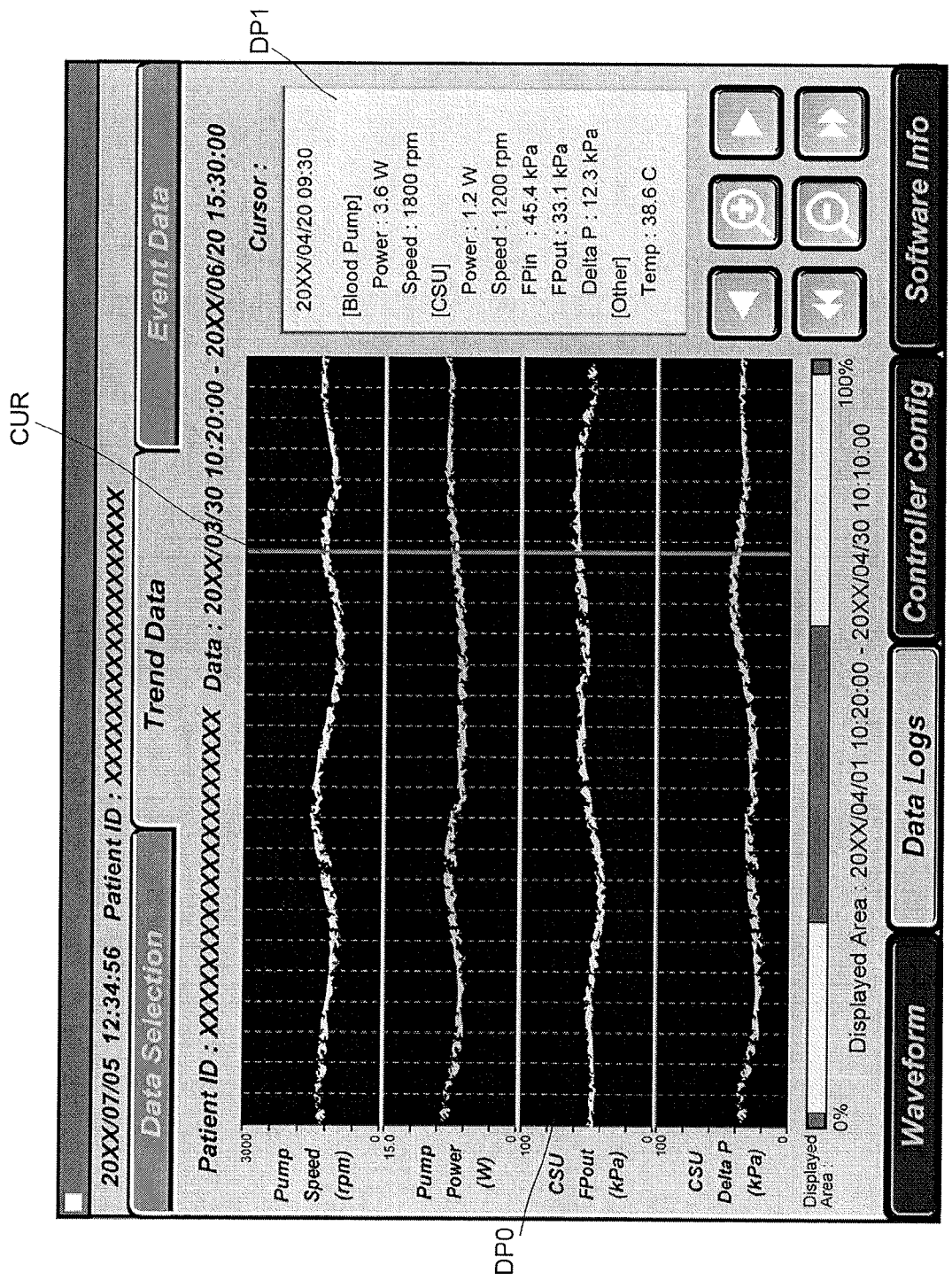
FIG. 13 is a view showing a first example of a display image displayed on an image display part of a data analyzer.

FIG. 13 shows a first example of a display image displayed on the image display part 240 of the data analyzer 200. That is, FIG. 13 shows one example where an image is formed using TR data acquired from the artificial heart control device 100 and the image is displayed on the image display part 240.

In the data analyzer 200, an image is formed by the image forming part 230 using TR data corresponding to a rotational speed and power consumption of the blood pump 20 and a flow passage pressure of the cool sealing unit 120 (an output pressure of the filter 126 shown in FIG. 4 in this example). As shown in FIG. 13, a flow passage pressure of the cool sealing unit 120 is displayed using TR data corresponding to an input pressure of the filter 126 shown in FIG. 4. In the data analyzer 200, by scrolling a display window, out of a waveform which is formed based on TR data accumulated for several days, a waveform which is formed based on TR data in a desired period is displayed in a waveform display region DP0. For example, in the waveform display region DP0, out of TR data accumulated for approximately 3 months in the past, a waveform which is formed based on TR data accumulated for 30 days is displayed. Here, values of operation data at a position of a cursor CUR which is movable within the waveform display region DP0 are displayed in a cursor position data display region DP1.

By acquiring TR data and by displaying the image shown in FIG. 13, for example, based on the TR data as described above, even when the artificial heart device 10 is operated for a long period, that is, several days to several months, an operation state of the artificial heart control device 100 and an operation state of the blood pump 20 can be periodically analyzed.

Figure 14:
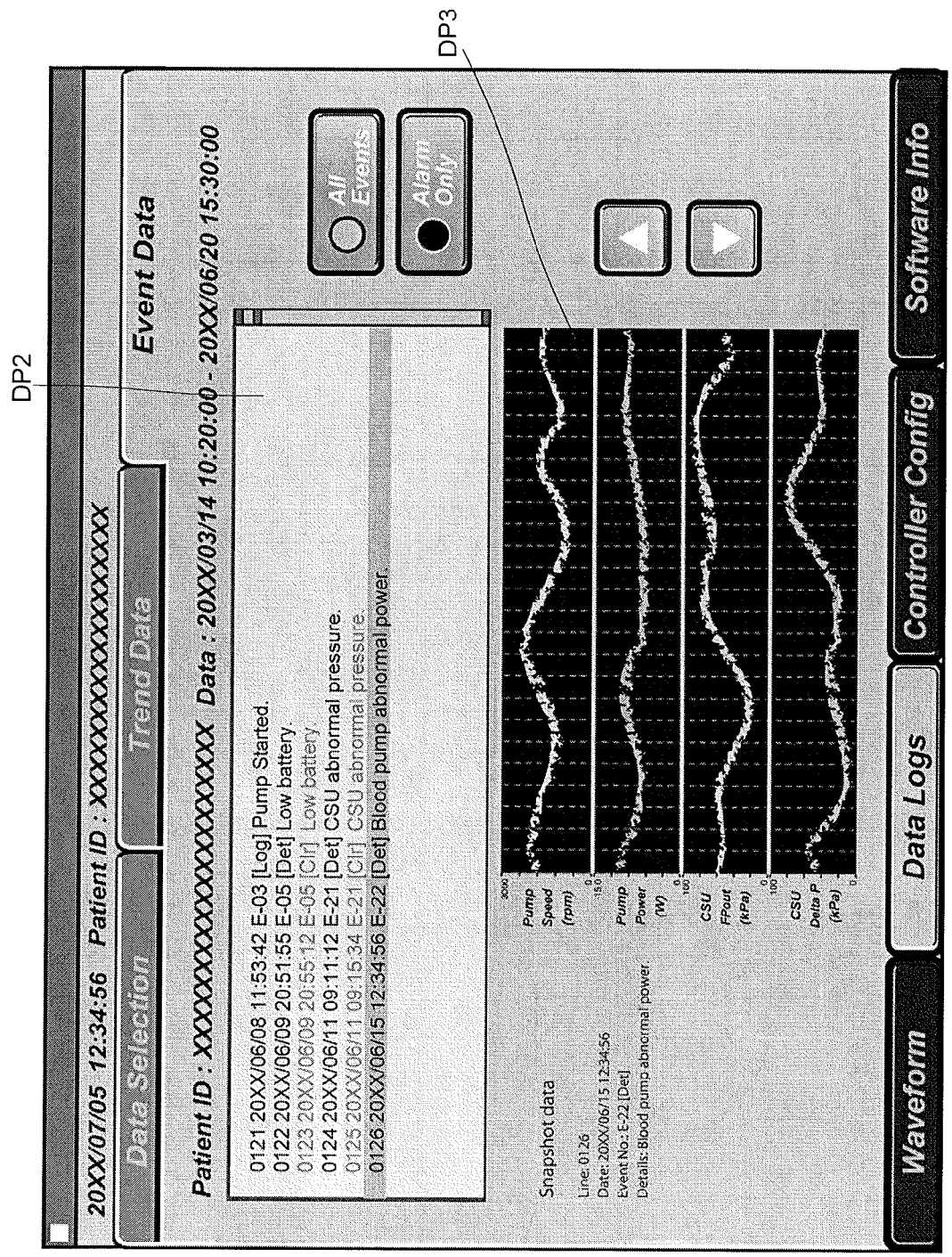
FIG. 14 is a view showing a second example of a display image displayed on the image display part of the data analyzer.

FIG. 14 shows a second example of a display image displayed on the image display part 240 of the data analyzer 200. That is, FIG. 14 shows one example where an image is formed using SS data acquired from the artificial heart control device 100 and the image is displayed on the image display part 240.

In the data analyzer 200, an image is formed on the image forming part 230 using EV data and SS data. As shown in FIG. 14, in an event state display region DP2, events which have occurred are displayed in chronological order based on EV data. For example, in the event state display region DP2, events are displayed in chronological order based on latest EV data out of EV data accumulated for approximately 3 months in the past. Here, corresponding to the event which is selected in the event state display region DP2 (reversely displayed event in FIG. 14), a waveform formed based on SS data for 5 seconds ranging from a point of time before event detection timing to a point of time after the event detection timing is displayed in an SS data display region DP3.

By acquiring SS data and by displaying the image shown in FIG. 14, for example, based on the SS data as described above, even when a certain occurrence cannot be analyzed using only the TR data, such a phenomenon can be analyzed by merely accumulating detailed data only on minimum required portions. Accordingly, even when the artificial heart device 10 is operated for a long period, that is, several days to several months, it becomes possible to understand an event occurrence state in more detail by analyzing the SS data.

Figure 15:
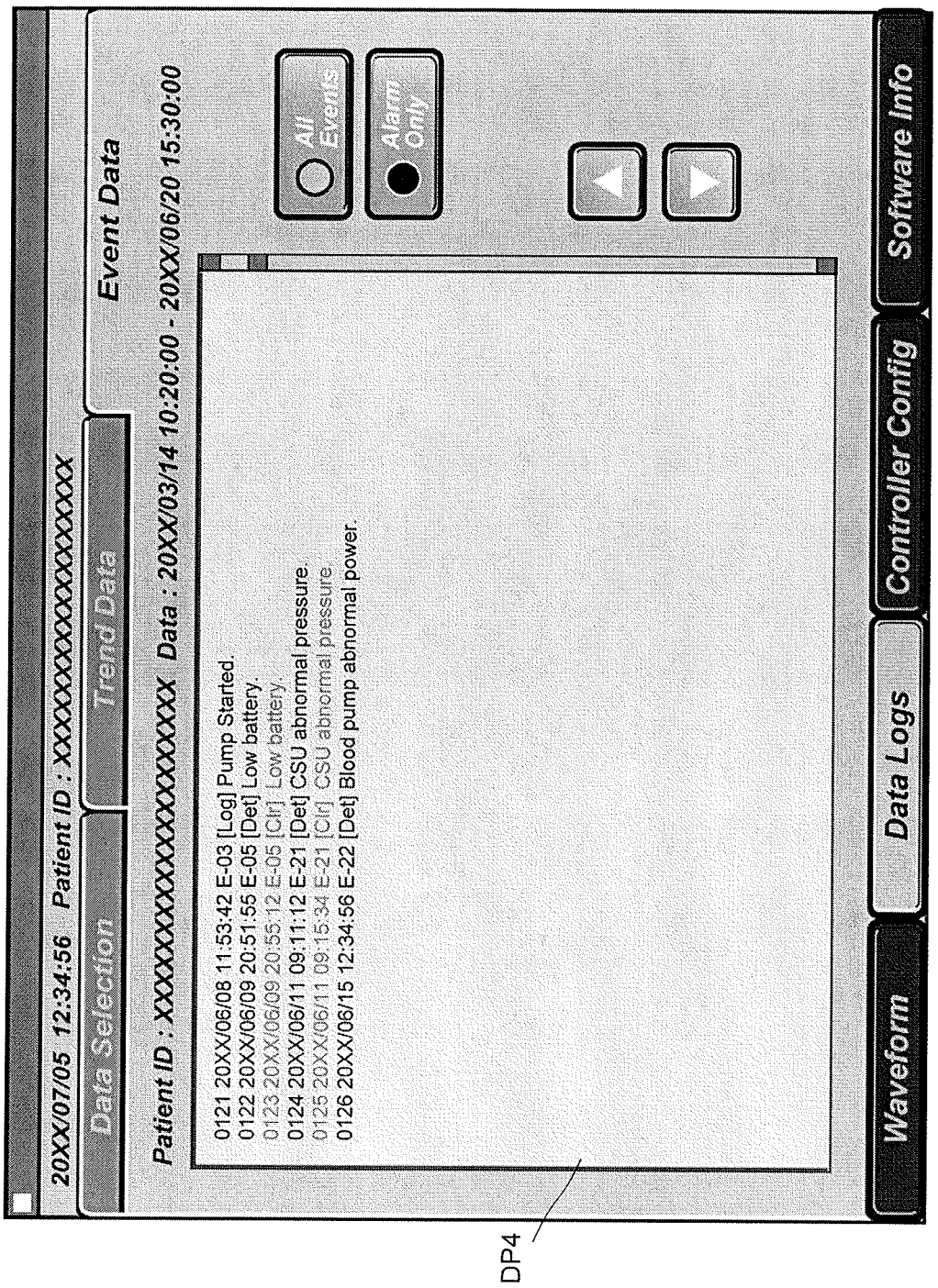
FIG. 15 is a view showing a third example of a display image displayed on the image display part of the data analyzer.

FIG. 15 shows a third example of a display image displayed on the image display part 240 of the data analyzer 200. That is, FIG. 15 shows one example where an image is formed using EV data acquired from the artificial heart control device 100 and the image is displayed on the image display part 240.

In the data analyzer 200, an image is formed by the image forming part 230 using EV data. As shown in FIG. 15, in an event data display region DP4, events which have occurred are displayed in chronological order based on EV data. In the event data display region DP4, for example, the respective events are displayed with colors corresponding to the kinds of events which are classified based on a place where an event occurs, a cause of the occurrence of the event, the degree of urgency of the event or the like. For example, in the event data display region DP4, events are displayed in chronological order based on latest EV data out of EV data accumulated for approximately 3 months in the past. Here, a display which conforms to an identification number corresponding to an event, a kind of event (for example, a detected event, a cleared event or a log event) (for example, [Det], [Clr], [Log]) is performed.

By acquiring EV data and by displaying the image shown in FIG. 15, for example, based on the EV data as described above, even when the artificial heart device 10 is operated for a long period, that is, several days to several months, it becomes possible to understand an event occurrence state.

Figure 16:
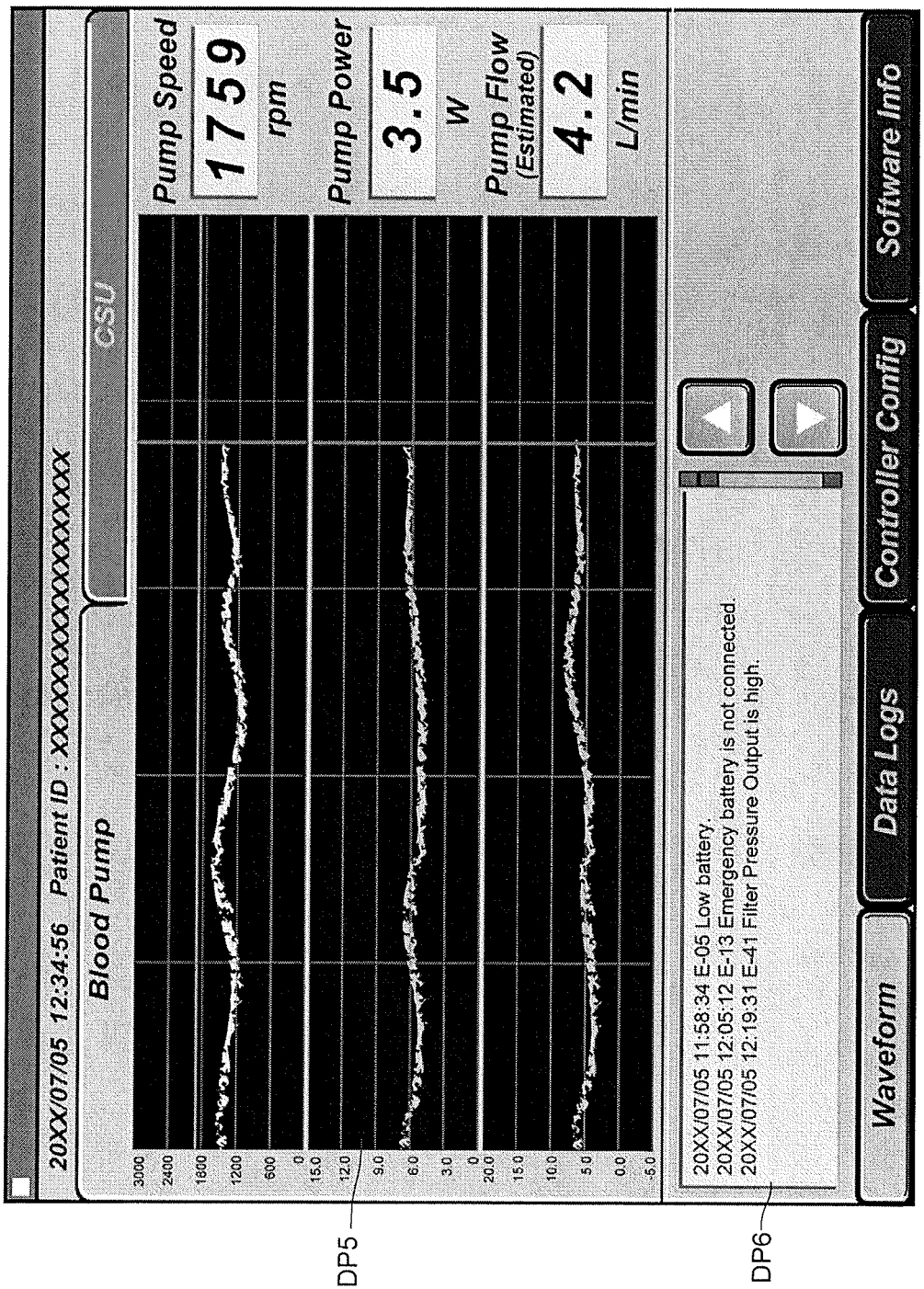
FIG. 16 is a view showing a fourth example of a display image displayed on the image display part of the data analyzer.

FIG. 16 shows a fourth example of a display image displayed on the image display part 240 of the data analyzer 200. That is, FIG. 16 shows one example where an image is formed using RT data acquired from the artificial heart control device 100 and the image is displayed on the image display part 240.

In the data analyzer 200, an image is formed by the image forming part 230 using RT data. As shown in FIG. 16, in a waveform display region DP5, waveforms are displayed based on the RT data transmitted from the artificial heart control device 100 virtually in real time. Here, it is desirable that a latest event occurrence state is displayed in an event state display region DP6. For example, in the event state display region DP6, events are displayed in chronological order based on the latest EV data.

In this manner, by acquiring RT data and by displaying the image shown in FIG. 16, for example, based on the RT data as described above, the data analyzer 200 is useful in monitoring a present operation state of the artificial heart control device 100 and the blood pump 20. For example, in a case where an event occurred in the past, it is possible to understand a present state of the event using the data analyzer 200 by referencing the RT data.

In all cases shown in FIG. 13 to FIG. 16, by displaying information on a patient, the identification number of the patient or the like corresponding to data stored in the management data storing part 168, it is possible to manage a state where a patient uses the artificial heart device 10 and a use state of respective parts of the artificial heart device 10 including the battery 130. Accordingly, a burden imposed on the patient can be reduced and, at the same time, reliability of the artificial heart device 10 can be enhanced.

As has been explained above, in this embodiment, data corresponding to states of the blood pump 20, the cool sealing unit 120, a power source of the artificial heart control device 100 and the like which constitute the artificial heart device 10 are stored in such a manner that the data are processed into plural kinds of data. Due to such processing, even after a patient leads a normal life with the blood pump 20 embedded in his body for a long period, the maintenance of the artificial heart device 10 becomes easy and hence, when an abnormality is detected in the blood pump 20 or the artificial heart control device 100, an operation of the blood pump 20 or the artificial heart control device 100 can be easily inspected.

[Modification]

Data on which data processing is performed by the data processing part 140 is not limited to data explained in conjunction with the above-mentioned embodiment. The data processing part 140 can apply first data processing, second data processing or third data processing to various data in the artificial heart device 10.

Figure 17:
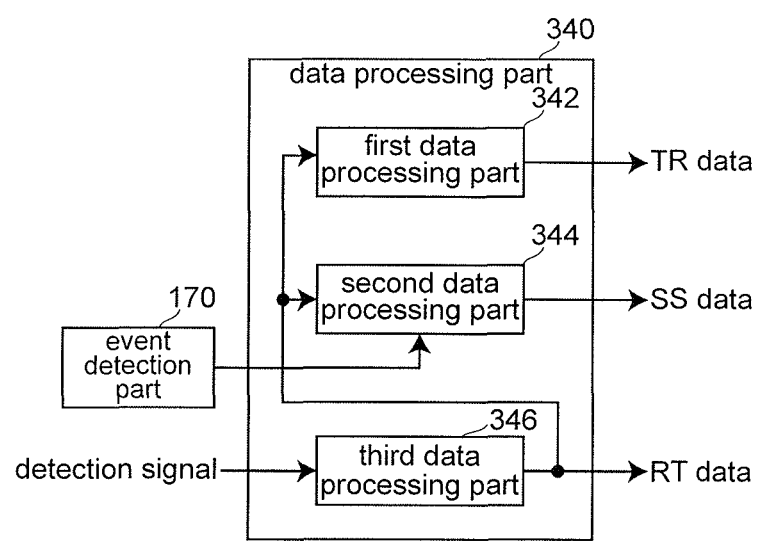
FIG. 17 is a block diagram showing the constitutional example of a data processing part according to a modification of the embodiment of the present invention.

FIG. 17 is a block diagram showing the constitutional example of a data processing part according to the modification of this embodiment. In FIG. 17, parts identical with the parts in FIG. 12 are given the same symbols and their repeated explanation is omitted when appropriate.

A data processing part 340 in this modification includes a first data processing part 342, a second data processing part 344 and a third data processing part 346. The third data processing part 346 possesses a function substantially equal to the function of the third data processing part 146 shown in FIG. 12. The first data processing part 342 performs first data processing on data to which processing performed by the third data processing part 346 is already applied, and outputs the processed data as TR data. The first data processing desirably includes calculation processing for acquiring an average value by calculation in a first period, calculation processing for acquiring a maximum value by calculation in a first period, calculation processing for acquiring a minimum value by calculation in a first period, and predetermined filter processing. That is, while the first data processing part 142 shown in FIG. 12 performs first data processing on detection signals transmitted from the various sensors or the like, the first data processing part 342 performs first data processing on RT data. In this manner, by carrying out the first data processing by making use of RT data acquired by processing carried out by the third data processing part 346, the constitution of the data processing part 340 can be simplified and miniaturized.

In the same manner, the second data processing part 344 performs second data processing on data to which processing performed by the third data processing part 346 is already applied, and outputs the processed data as SS data. The second data processing desirably includes calculation processing for acquiring an average value by calculation, calculation processing for acquiring a maximum value by calculation, calculation processing for acquiring a minimum value by calculation, and predetermined filter processing. That is, while the second data processing part 144 shown in FIG. 12 performs second data processing on detection signals transmitted from the various sensors or the like, the second data processing part 344 performs second data processing on RT data. In this manner, by applying the second data processing to RT data acquired by processing performed by the third data processing part 346, the constitution of the data processing part 340 can be simplified and miniaturized.

The artificial heart control device 100 shown in FIG. 5 may use the data processing part 340 shown in FIG. 17 in place of the data processing part 140. With the use of the data processing part 340, the constitution and the control of the data processing part can be simplified compared to the embodiment.

According to the embodiments or the modifications explained heretofore, following advantageous effects can be acquired, for example.

Firstly, the normal operations of the respective parts which constitute the artificial heart device 10 operated for a long period can be easily confirmed. Conventionally, there is no way but to confirm the normal operations of respective parts by a method which exhibits relatively low reliability such as an interview with a patient at the time of a periodic medical checkup about an occurrence state of an alarm or whether or not the patient feels abnormality in an operation of a blood pump, for example. To the contrary, according to this embodiment or the modification, operation states of the respective parts of the artificial heart device 10 are stored in the form of data in various modes, and the operation states can be referenced later whereby the infallibility of the artificial heart device at the time of normal use in the past can be confirmed.

Secondly, the above-mentioned embodiment or modification has an advantageous effect that it is possible to easily find out a cause of the occurrence of abnormality in respective parts which constitute the artificial heart device 10 or to facilitate the decision on a countermeasure to cope with such abnormality. Even in a case where there is a possibility that abnormality exists in the inside of the blood pump 20 at the time of detecting abnormality, when abnormality occurs temporarily, it may be determined that the measurement is abnormal due to the influence of electromagnetic waves or the like. If an abnormality occurrence state can be analyzed in such a state, the more appropriate countermeasure can be readily decided so that a burden imposed on a patient could be largely reduced.

Thirdly, the embodiment or the modification can acquire an advantageous effect that it is possible to understand a change in hemodynamics of a patient who leads a normal life with the blood pump 20 embedded in his body for a long period. TR data and RT data corresponding to an operation state of the blood pump 20 contains information on a rotational speed and power consumption of the blood pump 20 and hence, these data can be considered as data which reflect the hemodynamics of the patient. For example, by acquiring RT data and TR data on a patient in unit of a short period (1 pulse unit to several minutes) and a long period (one day to several months), these data can be medically used as information relating to the hemodynamics of the patient.

Fourthly, the embodiment or the modification can acquire an advantageous effect that it is possible to analyze the manner that a patient who leads a normal life with the blood pump 20 embedded in his body for a long period uses the artificial heart device. For example, when a battery is frequently mounted or removed by the patient, this behavior remains in a record and hence, it is possible for a doctor or the like to instruct the patient or wear of a connector portion of the battery can be avoided. Accordingly, abnormality can be easily detected in advance or can be easily prevented in advance or the decision of an exchange cycle can be easily decided whereby a lifetime of the artificial heart device 10 can be prolonged and abnormality occurrence probability can be lowered thus enhancing the reliability of the artificial heart device 10. Further, finding of a cause of abnormality, data control or the like becomes easy by associating information on a patient and identification numbers of a battery and constitutional element of the artificial heart device with each other.

Fifthly, the embodiment or the modification can acquire an advantageous effect that it is unnecessary to additionally provide cumbersome measuring equipment for the portable artificial heart control device 100 and hence, QOL of a patient can be enhanced. Accordingly, the patient can secure his life with no restriction without paying attention to storing of data.

The artificial heart control device according to the present invention and the like has been explained in conjunction with the above-mentioned embodiment and the modification heretofore. However, the present invention is not limited to the above-mentioned embodiment and the modification, and the present invention can be carried out in various modes without departing from the gist of the present invention, and following modifications are conceivable, for example.

(1) In the above-mentioned embodiment and the modification, the explanation has been made with respect to the case where a continuous flow type blood pump is used as a blood pump. However, the present invention is not limited to the blood pump of such a type, and the blood pump may be a pulsation flow type blood pump which imparts predetermined cycle to the flow of blood to be circulated or a magnetic floating type blood pump.

(2) The blood pump used in the above-mentioned embodiment or the modification may be realized by an AC motor which is driven using three-phase drive signals, a motor driven by drive signals other than three-phase drive signals, for example, or a DC motor.

(3) In the above-mentioned embodiment and the modification, the explanation has been made with respect to the case where the artificial heart control device includes the cool sealing unit. However, the present invention is not limited to such an artificial heart control device. For example, the artificial heart control device or the artificial heart device according to the present invention may not include the cool sealing unit. Further, the present invention is not limited to the constitution or the principle where cool sealing liquid is supplied to a bearing portion by the cool sealing unit.

(4) In the above-mentioned embodiment and the modification, the explanation has been made with respect to the case where the present invention is directed to the artificial heart device or the like. However, the present invention is not limited to such artificial heart device or the like. For example, the present invention may be directed to a software program in which processing steps of a control method of controlling the artificial heart device according to the present invention are described or a recording medium in which the software program is recorded.

EXPLANATION OF SYMBOLS

10: artificial heart device, 20: blood pump, 21: drive part, 22: pump part, 23: impeller, 24: pump casing, 25: inflow port, 26: outflow port, 27: mechanical seal part, 50: cable, 80: heart, 100: artificial heart control device, 110: blood pump control part, 120: cool sealing unit, 122: pump, 124: reservoir, 126: filter, 128: circulation passage, 130: battery, 140, 340: data processing part, 142, 342: first data processing part, 144, 344: second data processing part, 146, 346: third data processing part, 160: data storing part, 162: TR data storing part, 164: SS data storing part, 166: EV data storing part, 168: management data storing part, 170: event detection part, 180: manipulation part, 190: real-time clock control part, 200: data analyzer, 210: data analyzing processing part, 220: analyzed data storing part, 230: image forming part, 240: image display part, 300: external memory, 310: printer, CUR: cursor, DP0, DP5: waveform display region, DP1: cursor position data display region, DP2, DP6: event state display region, DP3: SS data display region, DP4: event data display region, SR1 to SR5: sensor

The invention claimed is:

1. An artificial heart device, comprising:
a blood pump configured to assist flow of blood in a heart of a patient;
a blood pump control part configured to control the blood pump;
at least one sensor configured to acquire operation data on the blood pump, operation data on a cool sealing unit configured to circulate lubrication fluid in the blood pump, biological data corresponding to a state of the patient or operation data on a power source which supplies electricity to the artificial heart device;
a first data processing part configured to perform first data processing on at least one of the operation data on the blood pump, the operation data on the cool sealing unit, the biological data and the operation data on the power source in each of a plurality of first periods;
a first data storing part configured to store, each time one of the plurality of first periods elapses, first processed data as trend data and, in association with first date-and-time data, the first processed data obtained from the first data processing performed in said first period, and the first date-and-time data corresponding to date and time at which the trend data is stored;
a second data processing part configured to perform second data processing on at least one of the operation data on the blood pump, the operation data on the cool sealing unit, the biological data and the operation data on the power source; and
a second data storing part configured to store snapshot data in association with second date-and-time data, the snapshot data being, out of second processed data obtained from the second data processing, the second processed data in a second period ranging from a point of time before detection timing of a predetermined event to a point of time after the detection timing of the predetermined event, and the second date-and-time data corresponding to date and time at which the snapshot data is stored, wherein
the trend data stored in the first data storing part and the snapshot data stored in the second data storing part are retrievable.

2. The artificial heart device according to claim 1, wherein the first data processing includes at least one of calculation processing for acquiring an average value by calculation in the first period, calculation processing for acquiring a maximum value by calculation in the first period, calculation processing for acquiring a minimum value by calculation in the first period, and predetermined filter processing.

3. The artificial heart device according to claim 1, wherein the second data processing includes at least one of calculation processing for acquiring an average value by calculation, calculation processing for acquiring a maximum value by calculation, calculation processing for acquiring a minimum value by calculation, and predetermined filter processing.

4. The artificial heart device according to claim 3, wherein the artificial heart device further comprises:
an event detecting part configured to detect the predetermined event based on at least one of the operation data on the blood pump, the operation data on the cool sealing unit, the biological data, the operation data on the power source, mounting and removal data which is updated at the time of mounting or removing the power source, and manipulation data on a manipulation part for controlling the artificial heart device.

5. The artificial heart device according to claim 1, wherein the artificial heart device further comprises:
an event detecting part configured to detect an event based on at least one of the operation data on the blood pump, the operation data on the cool sealing unit, the biological data, the operation data on the power source, mounting and removal data which is updated at the time of mounting or removing the power source, and manipulation data on a manipulation part for controlling the artificial heart device; and
a third data storing part configured to store event data in association with third date-and-time data,
the event data corresponding to the event detected by the event detecting part, and
the third date-and-time data corresponding to date and time at which the event is detected by the event detecting part, and wherein
the event data stored in the third data storing part is retrievable.

6. The artificial heart device according to claim 1, wherein the artificial heart device is configured to output at least one of the operation data on the blood pump, the operation data on the cool sealing unit, the biological data and the operation data on the power source.

7. The artificial heart device according to claim 1, wherein the artificial heart device further comprises a fourth data storing part configured to store, as management data, at least one of information on the patient, an identification number given to a constitutional element of the artificial heart device, the time the artificial heart device was used, an identification number given to the power source, the time the power source was used, and the number of times of charge to the power source, and
the management data stored in the fourth data storing part is retrievable.

8. The artificial heart device according to claim 1, wherein the artificial heart device further comprises:
the cool sealing unit configured to circulate the lubrication fluid in the blood pump; and
a circulation path along which the lubrication fluid is circulated.

* * * * *